United States Patent
Hamburger et al.

(10) Patent No.: US 10,869,474 B2
(45) Date of Patent: Dec. 22, 2020

(54) FUNGICIDAL COMPOSITIONS

(71) Applicants: UNIVERSITÄT BASEL, Basel (CH); FORSCHUNGSINSTITUT FÜR BIOLOGISCHEN LANDBAU (FIBL), Frick (CH)

(72) Inventors: Matthias Hamburger, Arlesheim (CH); Olivier Potterat, Aesch (CH); Justine Ramseyer, Porrentruy (CH); Hans-Jakob Schärer, Zeiningen (CH); Barbara Thürig, Riehen (CH); Lucius Tamm, Elfingen (CH); Thomas Oberhänsli, Nuglar (CH)

(73) Assignees: UNIVERSITÄT BASEL, Basel (CH); FORSCHUNGSINSTITUT FÜR BIOLOGISCHEN LANDBAU (FIBL), Frick (CH)

( * ) Notice: Subject to any disclaimer, the term of this patent is extended or adjusted under 35 U.S.C. 154(b) by 0 days.

(21) Appl. No.: 16/311,847

(22) PCT Filed: Jun. 20, 2017

(86) PCT No.: PCT/EP2017/065065
§ 371 (c)(1),
(2) Date: Dec. 20, 2018

(87) PCT Pub. No.: WO2017/220565
PCT Pub. Date: Dec. 28, 2017

(65) Prior Publication Data
US 2019/0200609 A1    Jul. 4, 2019

(30) Foreign Application Priority Data
Jun. 21, 2016 (EP) .................... 16175538

(51) Int. Cl.
*A01N 37/10* (2006.01)
*A01N 65/20* (2009.01)
(Continued)

(52) U.S. Cl.
CPC ............ *A01N 37/10* (2013.01); *A01N 37/06* (2013.01); *A01N 65/00* (2013.01); *A01N 65/08* (2013.01);
(Continued)

(58) Field of Classification Search
CPC ........ A01N 37/10; A01N 37/06; A01N 65/00; A01N 65/08; A01N 65/20; C07C 69/618; C07C 69/78
See application file for complete search history.

(56) References Cited

U.S. PATENT DOCUMENTS 6,090,752 A * 7/2000 Emerson ................ A01N 37/02
504/157
8,536,089 B2 * 9/2013 Walter .................... A01N 43/56
504/100
(Continued)

FOREIGN PATENT DOCUMENTS

| WO | WO-9956547 A1 * | 11/1999 | ............. A01N 37/02 |
| WO | WO 99/62334 A1 | 12/1999 | |
| WO | WO-2012077120 A2 * | 6/2012 | ............. A61K 8/345 |

OTHER PUBLICATIONS

Pastorova et al. Analytical Study of Free and Ester Bound Benzoic and Cinnamic Acids of Gum Benzoin Resins by GC-MS and HPLC-frit FAB-MS. Phytochemical Analysis, 1997, 8:63-73. (Year: 1997).*

(Continued)

*Primary Examiner* — Robert A Wax
*Assistant Examiner* — Olga V. Tcherkasskaya
(74) *Attorney, Agent, or Firm* — Medler Ferro Woodhouse & Mills PLLC

(57) ABSTRACT

The present invention relates to the use of a composition as a fungicide, wherein said composition comprises at least one compound of formula (I) or formula (II)

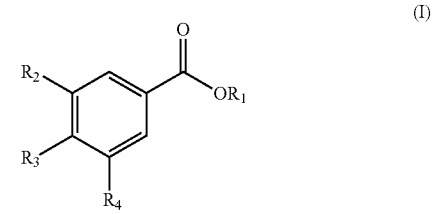

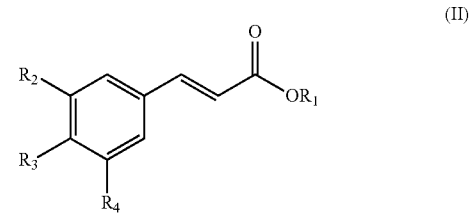

wherein

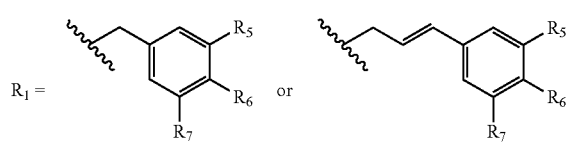

(Continued)

wherein
R$_2$, R$_3$, R$_4$, R$_5$, R$_6$ and R$_7$ are independently of each other H, OH or OCH$_3$.

26 Claims, No Drawings

(51) Int. Cl.
| | | |
|---|---|---|
| *A01N 65/00* | (2009.01) | |
| *A01N 37/06* | (2006.01) | |
| *A01N 65/08* | (2009.01) | |
| *C07C 69/618* | (2006.01) | |
| *C07C 69/78* | (2006.01) | |

(52) U.S. Cl.
CPC ............ *A01N 65/20* (2013.01); *C07C 69/618* (2013.01); *C07C 69/78* (2013.01)

(56) References Cited

U.S. PATENT DOCUMENTS

| | | | | |
|---|---|---|---|---|
| 9,538,755 | B2 * | 1/2017 | Walter | A01N 43/56 |
| 9,949,482 | B2 * | 4/2018 | Walter | A01N 43/56 |
| 10,405,548 | B2 * | 9/2019 | Walter | A01N 43/56 |
| 2008/0070785 | A1 * | 3/2008 | Walter | A01N 43/56 |
| | | | | 504/130 |
| 2014/0051736 | A1 * | 2/2014 | Walter | A01N 43/56 |
| | | | | 514/383 |
| 2017/0071205 | A1 * | 3/2017 | Walter | A01N 43/56 |
| 2018/0228157 | A1 * | 8/2018 | Walter | A01N 43/56 |
| 2018/0289005 | A1 * | 10/2018 | Hoffman | A01N 37/50 |
| 2019/0150455 | A1 * | 5/2019 | Silberstein | A01N 37/40 |

OTHER PUBLICATIONS

Custódio et al., "True and common balsams," *Brazilian Journal of Pharmacognosy* 22(6):1372-1383 (2012).
Khatkar et al., "Synthesis and antimicrobial evaluation of ferulic acid derivatives," *Research on Chemical Intermediates* 41(1):299-309 (2013).
Koga et al., "Synthesis and Antimycotic Activity of Cinnamyl Benzoate," *Journal of Fermentation and Bioengineering* 76(6):524-526 (1993).
Mahajan et al., "A facile microwave assisted synthesis and antimicrobial activities of naturally occurring (E)-cinnamyl (E)-cinnamates and (E)-aryl cinnamates," *Indian Journal of Chemistry* 46B:1459-1465 (2007).
Tawata et al., "Synthesis and Antifungal Activity of Cinnamic Acid Esters," *Bioscience, Biotechnology, and Biochemistry* 60(5):909-910 (1996).
Tuntipaleepun et al., "Antifungal and cytotoxic substances from the stem barks of *Desmos chinensis*," *Chinese Chemical Letters* 23:587-590 (2012).
Yanar et al., "In vitro antifungal activities of 26 plant extracts on mycelial growth of *Phytophthora infestans* (Mont.) de Bary," *African Journal of Biotechnology* 10(14):2625-2629 (2011).
International Search Report in PCT/EP2017/065065, dated Sep. 13, 2017.
Dagostin et al., "*Salvia officinalis* Extract Can Protect Grapevine Against *Plasmopara viticola*," Plant disease 94(5): 575-580 (2010).
Hovaneissian et al., "Analytical Investigation of Styrax and Benzoin Balsams by HPLC-PAD-fluorimetry and GC-MS," Phytochemical Analysis, 19: 301-310 (2008).
Isman et al., "Plant Natural Products as a Source of Developing Environmentally Acceptable Insecticides," chapter in: Ishaaya et al. (Eds.), Insecticides Design using Advanced Technologies, Springer-Verlag, Berlin Heidelberg pp. 235-248 (2007).
Morton et al., "A Short History of Fungicides," APS net Features. doi: 10.1094/APSnetFeature-2008-0308 (2008).
Scherf et al., "Efficacy of Leaf Extract Fractions of *Glycyrrhiza glabra* L. against Downey Mildew of Cucumber (*Pseudoperonospora cubensis*)," Eur. J. Plant Pathol. 143: 755-762 (2012).
Speiser et al., "Betriebsmittelliste," Research Institute of Organic Agriculture, Frick (2006).
Tamm et al., "Direct Control of Airborne Diseases," in: Finckh et al. (Eds.), "Plant Diseases and their Management in Organic Agriculture," APS Press, (2015).
Van-Zwieten et al., "Review of Impacts on Soil Biota Caused by Copper Residues from Fungicide Application," SuperSoil 3 (2004).
Vogt et al., "Antifugal Activity in vitro and in vivo of Extracts and Lignans Isolated from *Larrea divaricata* Cav. against Pytopathogenic fungus," Industrial Crops Prod., 42: 583-586 (2013).

* cited by examiner

FUNGICIDAL COMPOSITIONS

The present invention relates to fungicidal compositions and their applications in agriculture, and more particularly to fungicidal compositions that are particularly effective for the prevention of fungal damage and for the treatment of fungal diseases in plants and plant propagation material. Specifically, the present invention relates to fungicidal compositions comprising esters of benzoic acid and/or cinnamic acid or plant extracts comprising the same.

RELATED ART

Plant diseases have been controlled or reduced for many years by the application of pesticides including inorganic substances such copper, sulfur, potassium bicarbonate, hydrated lime or acidified clay minerals which are still frequently used (Tamm L., Speiser B. (2015) Direct control of airborne diseases, in: M. R. Finckh, et al. (Eds.), Plant diseases and their management in organic agriculture, APS Press, St. Paul, Minn., USA). A number of new organic chemistry classes have in the meantime been introduced as fungicides, including dithiocarbamates, benzimidazoles, imidazoles, pyrimidines, triazoles, anilides or strobilurines.

Due to concerns related to impacts on human health and the environment, there is growing demand to replace chemical pesticides by alternatives. Moreover, under more stringent regulations, many pesticides have already been banned or are under reconsideration. Others are still allowed, but their use should be reduced or avoided wherever possible. For example, copper is widely used in conventional, integrated and organic agriculture to control devastating plant diseases such as grapevine downy mildew (*Plasmopara viticola*), potato and tomato late blight (*Phytophthora infestans*), apple scab (*Venturia inaequalis*), and a wide range of other plant pathogens, even though copper should be replaced urgently as it has an unfavorable ecotoxicological profile (Van-Zwieten L., Merrington G., Van-Zwieten M. (2004) Review of impacts on soil biota caused by copper residues from fungicide application. SuperSoil 2004:3rd).

Control of pathogens by means of plant-derived plant protection products can be an effective, sustainable, and environmentally friendly method for pest management in integrated pest management (IPM) and organic farming systems (Isman M. B., Akhtar Y. (2007) Plant natural products as a source for developing environmentally acceptable insecticides, in: I. Ishaaya, et al. (Eds.), Insecticides design using advanced technologies, Springer-Verlag, Berlin Heidelberg. pp. 235-248). Natural organic compounds are often easily degraded in a natural environment, e.g. by degradation by UV-light, and are thus less likely to accumulate in the environment or to cause residues on food. Extracts of selected plants, such as *Glycyrrhiza glabra* (Scherf A., Treutwein J., Kleeberg H., Schmitt A. (2012) Efficacy of leaf extract fractions of *Glycyrrhiza glabra* L. against downy mildew of cucumber (*Pseudoperonospora cubensis*). Eur. J. Plant Pathol. 134:755-762), *Salvia officinalis* (Dagostin S., Formolo T., Giovannini O., Pertot I., Schmitt A. (2010) *Salvia officinalis* extract can protect grapevine against *Plasmopara viticola*. Plant disease 94:575-580) or *Larrea divaricata* (Vogt V., Cifuente D., Tonn C., Sabini L., Rosas S. (2013) Antifungal activity in vitro and in vivo of extracts and lignans isolated from *Larrea divaricata* Cav. against phytopathogenic fungus. Ind. Crops Prod. 42:583-586) have been shown to be active against plant diseases. Yet, still very few plant extracts against a limited range of diseases have been developed for commercial use and, in line, only very few are registered, for example, in Switzerland (Speiser B., Tamm L., Roggli M., Berner A., Bickel R., Maurer V., Schneider C., Chevillat V. (2016) Betriebsmittelliste 2016 Research Institute of Organic Agriculture, Frick). In conclusion, there is an ever growing need for plant protection products, and in particular for plant-derived plant protection products.

Siam benzoin is the resin produced by the bark of *Styrax tonkinensis* (Pierre) Craib ex Hartwich (Styracaceae), a tree growing across Thailand, Laos, Cambodia, and Vietnam. Sumatra benzoin is the resin obtained from the closely related species *Styrax benzoin* Dryand and/or *Styrax paralleloneurum* Perk (synonym *Styrax sumatranus* J J S) growing in Indonesia. Siam benzoin mainly contains benzoic acid and esters thereof, while benzoic acid derivatives are partly replaced in Sumatra benzoin by cinnamic acid in free and esterified forms such as p-coumaryl cinnamate (Hovaneissian M., Archier P., Mathe C., Culioli G., Vieillescazes C. (2008) Analytical investigation of *styrax* and benzoin balsams by HPLC-PAD-fluorimetry and GC-MS. Phytochemical Analysis 19:301-310 (Hovaneissian et al., 2008). Both balsamic resins have been traditionally used in perfumes and as incenses. More recently, cosmetic applications and medicinal properties such as positive effects on the human immune system as well as neuroprotective, neuroregenerative and anti-inflammatory properties have been described (US2004258712, WO2005/120528, WO2009/034366, US2012027868). WO1999/056547 describes herbicidal compositions and suggests the use of 3-phenyl-2-propen-1-ol benzoates as herbicides.

Balsam of Peru is a balsam derived from the tree *Myroxylon balsamum* (L.) Harms var. *pereirae* Royle (Fabaceae) growing in South America. Its main constituents are benzoic and cinnamic acid esters, in particular benzyl benzoate and benzyl cinnamate. Balsam of Peru has been used as a flavouring agent and in toiletries and perfumes. Balsam of Peru has been also traditionally used for the topical treatment of wounds.

SUMMARY OF THE INVENTION

We have surprisingly found that extracts from Sumatra benzoin, Siam benzoin, and Balsam of Peru exhibit antifungal activity against plant pathogenic fungi. In particular, we have surprisingly found a strong inhibitory activity of Siam benzoin and Sumatra benzoin against the plant pathogens *P. viticola*, *V. inaequalis* and *P. infestans* and of balsam of Peru against *P. viticola* as shown by in vitro assays. Furthermore, we have identified as active constituents, in particular, coniferyl benzoate, p-coumaryl cinnamate, and benzyl cinnamate. Semi-controlled bioassays with grapevine, apple and tomato seedlings confirmed furthermore efficacy of Siam benzoin and Sumatra benzoin as well as their active constituents against downy mildew caused by *P. viticola*, apple scab caused by *V. inaequalis*, *Marssonina* leaf drop caused by *M. coronaria* and late blight caused by *P. infestans*. In addition, the efficacy of Siam benzoin against *P. viticola* was confirmed under field conditions after appropriate formulation. Moreover, an effect against grapevine powdery mildew caused by the obligate biotroph *Oidium tuckeri* was demonstrated in the field.

Thus, in a first aspect, the present invention provides for the use of a composition as a fungicide, wherein said composition comprises at least one compound of formula (I) or formula (II)

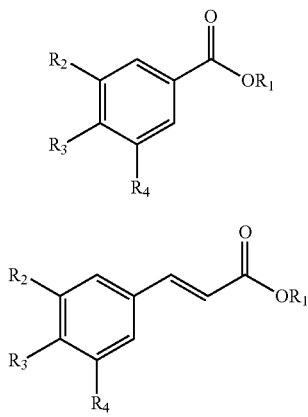

(I)

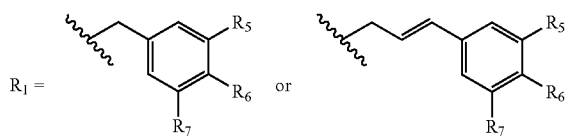

(II)

wherein

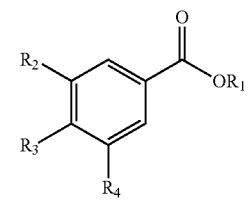

$R_1 =$ or wherein $R_2$, $R_3$, $R_4$, $R_5$, $R_6$ and $R_7$ are independently of each other H, OH or $OCH_3$.

In a further aspect, the present invention provides for the use as a fungicide of a compound of formula (I) or formula (II)

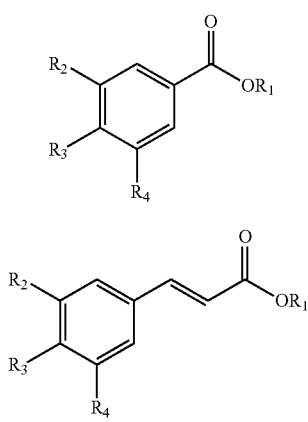

(I)

(II)

wherein

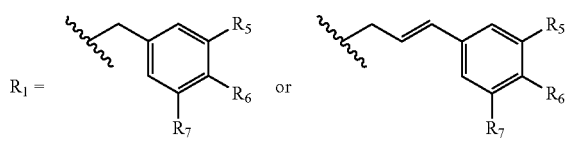

wherein $R_2$, $R_3$, $R_4$, $R_5$, $R_6$ and $R_7$ are independently of each other H, OH or $OCH_3$.

In another aspect, the present invention provides for the use as a fungicide of a plant extract, wherein said plant extract comprises at least one compound of formula (I) or formula (II)

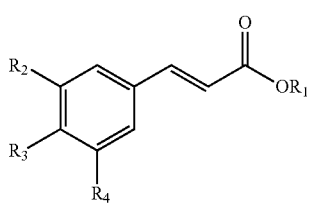

(I)

(II)

wherein

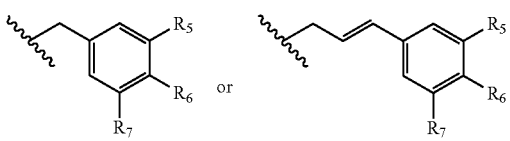

$R_1 =$ or wherein $R_2$, $R_3$, $R_4$, $R_5$, $R_6$ and $R_7$ are independently of each other H, OH or $OCH_3$.

In a further aspect, the present invention provides for the use of a composition as a fungicide, wherein said composition comprises at least one plant extract, wherein said at least one plant extract is an extract from a plant of the family of Styracaceae or a plant of the genus *Myroxylon*. In again a further aspect, the present invention provides for the use of a composition as a fungicide, wherein said composition comprises an extract of Sumatra benzoin, Siam benzoin and Balsam of Peru. In again a further aspect, the present invention provides for the use of a composition as a fungicide, wherein said composition comprises an extract of Sumatra benzoin. In again a further aspect, the present invention provides for the use of a composition as a fungicide, wherein said composition comprises an extract of Siam benzoin. In again a further aspect, the present invention provides for the use of a composition as a fungicide, wherein said composition comprises an extract of Balsam of Peru.

In another aspect, the present invention provides for the use as a fungicide of at least one plant extract, wherein said at least one plant extract is an extract from a plant of the family of Styracaceae or a plant of the genus *Myroxylon*. In another aspect, the present invention provides for the use as a fungicide of at least one plant extract, wherein said at least one plant extract is an extract from a plant of the family of Styracaceae. In another aspect, the present invention provides for the use as a fungicide of at least one plant extract, wherein said at least one plant extract is an extract from a plant of the genus *Myroxylon*. In a further aspect, the present invention provides for the use as a fungicide of at least one plant extract of Sumatra benzoin, Siam benzoin and Balsam of Peru. In a further aspect, the present invention provides for the use as a fungicide of at least one plant extract of Sumatra benzoin. In a further aspect, the present invention provides for the use as a fungicide of at least one plant extract of Siam benzoin. In a further aspect, the present invention provides for the use as a fungicide of at least one plant extract of Balsam of Peru.

Further aspects and embodiments of the present invention will be become apparent as this description continues.

DETAILED DESCRIPTION OF THE INVENTION

Unless defined otherwise, all technical and scientific terms used herein have the same meanings as commonly understood by one of ordinary skill in the art to which this invention belongs.

As used herein "a" or "an" means one or more, unless specifically indicated to mean only one.

The composition of the present invention can be used, in particular, to treat a plant, plant propagation material—such as a seed, cutting, rhizome, tuber, or bulb, for example—or soil to ameliorate or prevent damage due to infections with plant fungal pathogens.

The treatment of a plant, plant propagation material or soil with a composition of the present invention can be accomplished in several ways. The inventive composition may be applied directly to a plant seed, or to soil in which the seed is to be planted, for example, at the time of planting along with the seed. Alternatively, it may be applied to the soil after planting and germination, or to the foliage of the plant after emergence.

The term "horticultural crop" as used herein is intended to mean tree, bush and perennial vine fruits; perennial bush and tree nuts; vegetables (roots, tubers, shoots, stems, leaves, fruits and flowers of edible and mainly annual plants); aromatic and medicinal foliage, flowers, seeds and roots (from annual or perennial plants); cut flowers, potted ornamental plants, and bedding plants (involving both annual or perennial plants); trees, shrubs, turf and ornamental grasses propagated and produced in nurseries for use in landscaping or for establishing fruit orchards or other crop production units.

The term "field crops" as used herein is intended to mean any of the herbaceous plants cultivated on a large scale in cultivated fields, primarily a grain crop, a forage crop, a sugar crop, an oil crop, a root crop or a fiber crop.

The term "fruit crop" as used herein is intended to mean a perennial, edible crop where the economic product is the fruit or is derived thereof.

When it is said that "an effective amount" of a composition according to the invention is used, it is meant that a sufficient amount of the at least one compound of formula (I) or formula (II) comprised in the inventive composition is applied to the plant, its propagation material or soil to achieve either an increase in the yield and/or the vigor of the plant, or to control a fungal infection, typically and preferably of the plant or its propagation material, preferably of the plant.

Accordingly, the expression "controlling a fungal infection" or "controlling a plant fungal pathogen" as used herein refers to invoking one or more of the following effects: (i) inhibition or arrest of fungal growth, including, reducing the rate of fungal growth or causing complete fungal growth arrest; (ii) reduction of the fungal infection incidence; (iii) reduction in fungal infection severity; and/or (iv) relief, to some extent, of one or more symptoms associated with fungal infections. By "fungal infection incidence", typically and preferably, is meant the percentage of leaves or fruit of a given plant showing symptoms of fungal infection. Assessment is known by the skilled in the art and typically made in comparison with leaves of control and non-treated plants. By "fungal infection severity", typically and preferably, is meant the percentage of leave, root or fruit area covered by lesions caused by said fungal disease. Assessment is known by the skilled in the art and typically made in comparison with leaves, roots or fruit of control and non-treated plants. "Symptoms associated with fungal infections" are, typically and preferably, yield losses, such as a reduced yield of tomatoes, grapes or apples, or a decrease in vigor of the plant.

The term "plant extract" as used herein is intended to mean any composition which is extracted from a plant or plant part by conventional techniques, wherein the term "plant part" comprises typically and preferably bark, wood, leaves, roots, flower buds and/or resin of said plant. Procedures and techniques of extraction and the solvents or solvent mixtures used for said extraction are known to the skilled person in the art and are described, for example in WO2005/120528. Solvents or mixtures of solvents, typically and preferably, include water, lower alcohols such as methanol or ethanol, esters, ethers, amines, acids, polyols, alkanes or halogenated or chlorinated alkanes, and hereby protic solvents thereof such as water, alcohols, acids, primary and secondary amines and aprotic solvents thereof such as acetonitrile, DMF or DMSO. Preferred solvents for extraction are typically water, methanol, ethanol, pentane, hexane, heptane, petrol ether, acetone, chloroform, polyethylene glycol, dichloromethane, DMSO or ethyl acetate and mixtures thereof. Plants or plant parts suitable for extraction for producing a plant extract according to the invention typically and preferably have a content of at least one compound of formula (I) or formula (II), wherein said content of at least one compound of formula (I) or formula (II) is at least 1% by weight or wherein said content of the sum of all of said at least one compound of formula (I) and formula (II) is at least 1% by weight. Preferably, plants or plant parts suitable for extraction for producing a plant extract according to the invention typically and preferably have a content of at least 1% by weight of at least one compound of formula (I) or formula (II). Further preferably, plants or plant parts suitable for extraction for producing a plant extract according to the invention typically and preferably have a content of at least one compound of formula (I) or formula (II), wherein said content of at least one compound of formula (I) or formula (II) is more than 3% by weight or wherein said content of the sum of all of said at least one compound of formula (I) and formula (II) is more than 3% by weight. Again further preferably, plants or plant parts suitable for extraction have a content of more than 3% by weight of a compound of formula (I) or formula (II).

The term "resin", as used herein and referring to the use as a fungicide of the plant extract in accordance with the present invention includes pure resins, gum-resins, oleo-gum-resins and balsams. Typically, said resin comprises at least 2% (w/w) of a compound of formula (I) or formula (II) or comprises at least 2% (w/w) by the sum of all of said at least one compound of formula (I) and formula (II), preferably said resin comprises at least 4% (w/w) of a compound of formula (I) or formula (II) or comprises at least 4% (w/w) by the sum of all of said at least one compound of formula (I) and formula (II). Typically and preferably, said resin comprises at least 2% (w/w) of compound 1, compound 2, compound 3, compound 4 or compound 5, or comprises at least 2% (w/w) by the sum of all of said compound 1, compound 2, compound 3, compound 4 or compound 5. Further preferably said resin comprises at least 4% (w/w) of compound 1, compound 2, compound 3, compound 4 or compound 5 or comprises at least 4% (w/w) by the sum of all of said compound 1, compound 2, compound 3, compound 4 and compound 5.

The term "Siam benzoin" as used herein refers to resin obtained from the bark of *Styrax tonkinensis* (Pierre) Craib ex Hartwich (Styracaceae). Siam benzoin is abbreviated herein as "SB".

The term "Sumatra benzoin" as used herein refers to resin obtained from the bark of *Styrax benzoin* Dryand and/or *Styrax paralleloneurum* Perk (synonym *Styrax sumatranus* J J S). Sumatra benzoin is abbreviated herein as "SumB".

The term "Balsam of Peru" as used herein refers to a balsam obtained from the bark of *Myroxylon balsamum* Harms var. *pereirae* Royle (synonyms *Myrospermum pereirae* Royle, *Myroxylon pereirae* (Royle) Klotzsch, *Toluifera pereirae* (Royle) Baill.) (Fabaceae). Balsam of Peru is abbreviated as "BP".

Thus, in a first aspect, the present invention provides for the use of a composition as a fungicide, wherein said composition comprises at least one compound of formula (I) or formula (II)

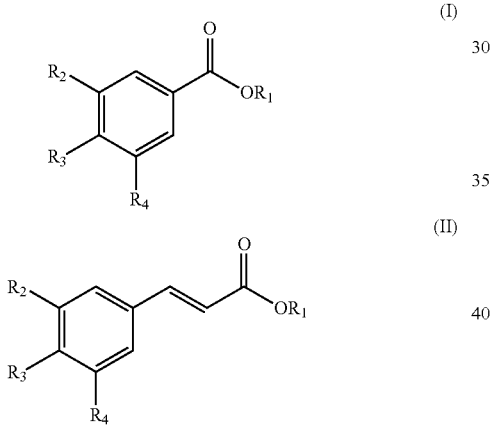

wherein

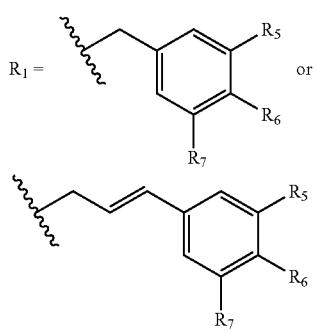

wherein $R_2$, $R_3$, $R_4$, $R_5$, $R_6$ and $R_7$ are independently of each other H, OH or $OCH_3$.

In a preferred embodiment, each of $R_5$, $R_6$ and $R_7$ are independently of each other H, OH or $OCH_3$. In a further preferred embodiment at most two of $R_5$, $R_6$ and $R_7$ are independently of each other OH or $OCH_3$. In again a further preferred embodiment $R_2$, $R_3$ and $R_4$ are each H. In another preferred embodiment, said $R_6$ is OH. In a further preferred embodiment, said $R_7$ is $OCH_3$. In again a further preferred embodiment, said $R_6$ is OH and said $R_7$ is $OCH_3$.

In a preferred embodiment, said composition comprises at least one compound of formula (I)

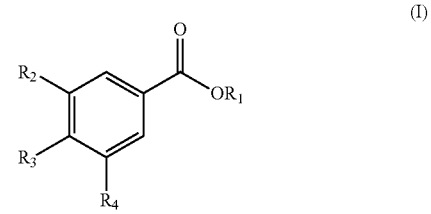

wherein

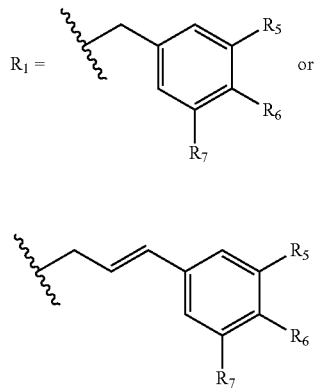

wherein $R_2$, $R_3$, $R_4$, $R_5$, $R_6$ and $R_7$ are independently of each other H, OH or $OCH_3$.

In a preferred embodiment, each of $R_5$, $R_6$ and $R_7$ are independently of each other H, OH or $OCH_3$. In a further preferred embodiment at most two of $R_5$, $R_6$ and $R_7$ are independently of each other OH or $OCH_3$. In again a further preferred embodiment $R_2$, $R_3$ and $R_4$ are each H. In another preferred embodiment, said $R_6$ is OH. In a further preferred embodiment, said $R_7$ is $OCH_3$. In again a further preferred embodiment, said $R_6$ is OH and said $R_7$ is $OCH_3$.

In a preferred embodiment, said composition comprises at least one compound of formula (I)

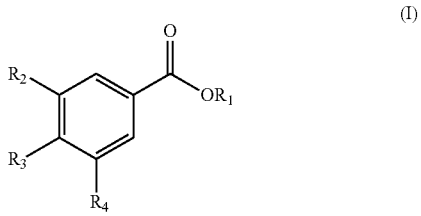

wherein

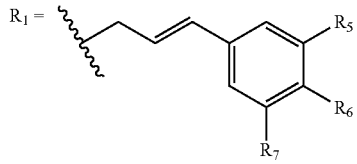

wherein

R$_2$, R$_3$, R$_4$, R$_5$, R$_6$ and R$_7$ are independently of each other H, OH or OCH$_3$.

In a preferred embodiment, each of R$_5$, R$_6$ and R$_7$ are independently of each other H, OH or OCH$_3$. In a further preferred embodiment at most two of R$_5$, R$_6$ and R$_7$ are independently of each other OH or OCH$_3$. In again a further preferred embodiment R$_2$, R$_3$ and R$_4$ are each H. In another preferred embodiment, said R$_6$ is OH. In a further preferred embodiment, said R$_7$ is OCH$_3$. In again a further preferred embodiment, said R$_6$ is OH and said R$_7$ is OCH$_3$.

In a preferred embodiment, said composition comprises at least one compound of formula (II)

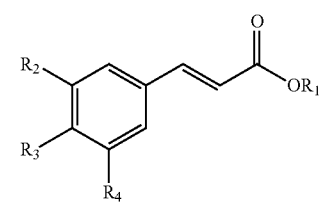

wherein

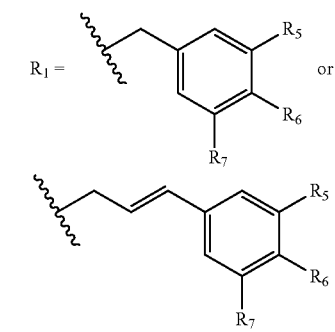

wherein

R$_2$, R$_3$, R$_4$, R$_5$, R$_6$ and R$_7$ are independently of each other H, OH or OCH$_3$.

In a preferred embodiment, each of R$_5$, R$_6$ and R$_7$ are independently of each other H, OH or OCH$_3$. In a further preferred embodiment at most two of R$_5$, R$_6$ and R$_7$ are independently of each other OH or OCH$_3$. In again a further preferred embodiment R$_2$, R$_3$ and R$_4$ are each H. In another preferred embodiment, said R$_6$ is OH. In a further preferred embodiment, said R$_7$ is OCH$_3$. In again a further preferred embodiment, said R$_6$ is OH and said R$_7$ is OCH$_3$.

In a preferred embodiment, said composition comprises at least one compound of formula (II)

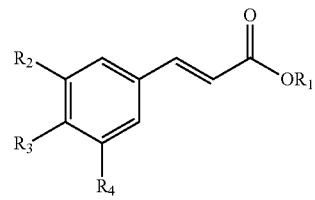

wherein

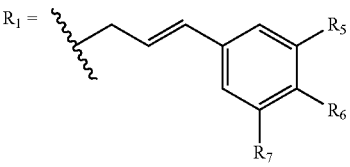

wherein

R$_2$, R$_3$, R$_4$, R$_5$, R$_6$ and R$_7$ are independently of each other H, OH or OCH$_3$.

In a preferred embodiment, each of R$_5$, R$_6$ and R$_7$ are independently of each other H, OH or OCH$_3$. In a further preferred embodiment at most two of R$_5$, R$_6$ and R$_7$ are independently of each other OH or OCH$_3$. In again a further preferred embodiment R$_2$, R$_3$ and R$_4$ are each H. In another preferred embodiment, said R$_6$ is OH. In a further preferred embodiment, said R$_7$ is OCH$_3$. In again a further preferred embodiment, said R$_6$ is OH and said R$_7$ is OCH$_3$.

In a very preferred embodiment, said at least one compound of formula (I) or formula (II) is selected from compound 1 (coniferyl benzoate), 2 (p-coumaryl cinnamate), 3 (benzyl cinnamate), 4 (benzyl benzoate) and 5 (cinnamyl cinnamate).

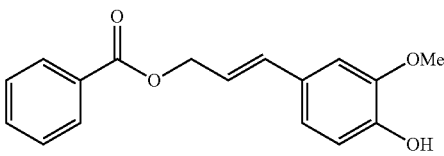

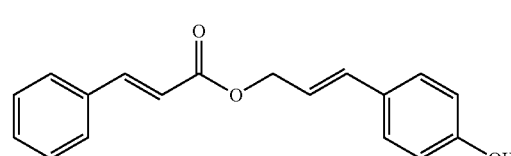

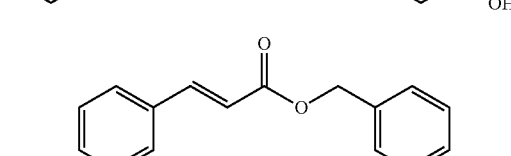

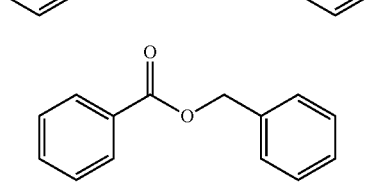

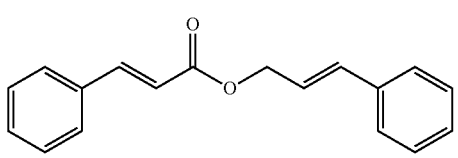

In a further very preferred embodiment, said at least one compound of formula (I) or formula (II) is compound 1 (coniferyl benzoate) or compound 2 (p-coumaryl cinnamate) or compound 3 (benzyl cinnamate)

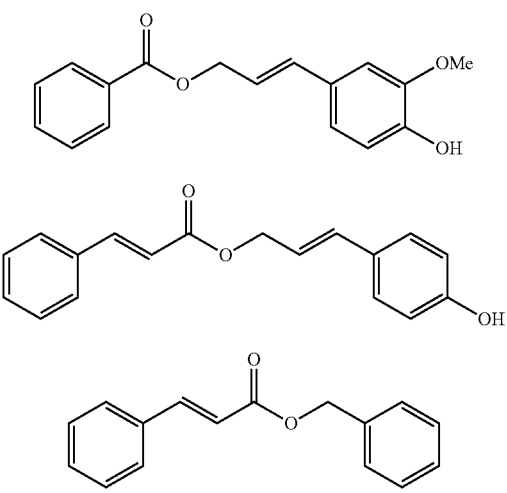

In another very preferred embodiment, said at least one compound of formula (I) or formula (II) is compound 1 (coniferyl benzoate). In another very preferred embodiment, said at least one compound of formula (I) or formula (II) is 2 (p-coumaryl cinnamate). In another very preferred embodiment, said at least one compound of formula (I) or formula (II) is 3 (benzyl cinnamate). In another very preferred embodiment, said at least one compound of formula (I) or formula (II) is 4 (benzyl benzoate). In another very preferred embodiment, said at least one compound of formula (I) or formula (II) is 5 (cinnamyl cinnamate).

In another very preferred embodiment, said composition comprises at least one, typically and preferably exactly one, plant extract, and wherein said plant extract comprises said at least one compound of formula (I) or formula (II). In another preferred embodiment, said at least one plant extract is an extract from a plant of the family of Styracaceae or a plant of the genus *Myroxylon*. In a preferred embodiment, said at least one plant extract is an extract from a plant of the genus *Styrax* or a plant of the genus *Myroxylon*.

In another very preferred embodiment, said at least one plant extract is an extract from a plant of the genus *Styrax* or a plant of the genus *Myroxylon*, and wherein said plant of the genus *Styrax* is selected from the species *Styrax tonkinensis, Styrax benzoin, Styrax paralleloneurum, Styrax hypoglauca* and *Styrax cascarifolia* or a subspecies or variety thereof, and wherein said plant of the genus *Myroxylon* is selected from the species *Myroxylon balsamum* and *Myroxylon peruiferum*.

In a preferred embodiment, said at least one plant extract is an extract from a plant of the genus *Styrax*, and preferably said plant of the genus *Styrax* is selected from the species *Styrax tonkinensis, Styrax benzoin, Styrax paralleloneurum, Styrax hypoglauca* and *Styrax cascarifolia* or a subspecies or variety thereof, and wherein further preferably said plant of the genus *Styrax* is selected from the species *Styrax tonkinensis, Styrax benzoin* and *Styrax paralleloneurum* or a subspecies or variety thereof.

In a further preferred embodiment, said at least one plant extract is an extract from a plant of the genus *Myroxylon*, and wherein preferably said plant of the genus *Myroxylon* is selected from the species *Myroxylon balsamum* and *Myroxylon peruiferum*.

In a very preferred embodiment, said at least one plant extract is an extract from a plant of the genus *Styrax*, and wherein said plant of the genus *Styrax* is selected from the species *Styrax tonkinensis, Styrax benzoin, Styrax paralleloneurum, Styrax hypoglauca* and *Styrax cascarifolia* or a subspecies or variety thereof, and wherein preferably said plant of the genus *Styrax* is selected from the species *Styrax tonkinensis, Styrax benzoin* and *Styrax paralleloneurum* or a subspecies or variety thereof.

In a further very preferred embodiment, said at least one plant extract is an extract from a plant of the genus *Myroxylon*, and wherein said plant of the genus *Myroxylon* is selected from the species *Myroxylon balsamum* and *Myroxylon peruiferum*.

In a very preferred embodiment, said at least one plant extract is an extract from a plant of the genus *Styrax*, and wherein said plant of the genus *Styrax* is selected from the species *Styrax tonkinensis, Styrax benzoin, Styrax paralleloneurum, Styrax hypoglauca* and *Styrax cascarifolia*, and wherein preferably said plant of the genus *Styrax* is selected from the species *Styrax tonkinensis, Styrax benzoin* and *Styrax paralleloneurum*.

In a further very preferred embodiment, said at least one plant extract is an extract of *Styrax tonkinensis, Styrax benzoin* or *Myroxylon balsamum*.

In a preferred embodiment, said at least one plant extract is an extract of bark, wood, leaves, roots, flower buds or resin of said plant. In a further very preferred embodiment, said at least one plant extract is an extract of a resin of said plant. In a further very preferred embodiment, said at least one plant extract is an extract of a resin of Siam benzoin or Sumatra benzoin or Balsam of Peru. In a further very embodiment, said at least one plant extract is an extract of a resin of Siam benzoin. In a further very embodiment, said at least one plant extract is an extract of a resin of Sumatra benzoin. In a further very embodiment, said at least one plant extract is an extract of a resin of Balsam of Peru.

In a further embodiment, said plant extract is an extract of bark, wood, leaves, roots, flower buds or resin of said plant with a protic solvent; wherein preferably said plant extract is an resin extract of said plant with a protic solvent, and further preferably wherein said protic solvent is water, methanol or ethanol, again further preferably methanol or ethanol. In a further embodiment, said plant extract is an ethanol extract from resin of said plant.

In a further embodiment, said plant extract is an extract of bark, wood, leaves, roots, flower buds or resin of said plant with an aprotic solvent; wherein preferably said plant extract is an extract of resin of said plant with a aprotic solvent, and further preferably wherein said aprotic solvent is selected from petroleum ether, hexane, heptane, acetone, ethyl acetate, DMSO, dichloromethane or chloroform, and wherein further preferably said plant extract is a petroleum ether extract from resin of said plant.

In a further embodiment, said at least one plant extract is a petroleum ether extract or an ethanol extract or a DMSO extract of bark, wood, leaves, roots, flower buds or resin of said plant; and wherein preferably said plant extract is a petroleum ether extract or a DMSO extract or an ethanol extract of resin of said plant. In a further very preferred embodiment, said plant extract is a petroleum ether extract or an ethanol extract of a resin of said plant.

In a further embodiment, said use as a fungicide of the inventive compositions, compounds and plant extracts is for controlling a plant fungal pathogen, wherein preferably said plant fungal pathogen is selected from (i) oomycetes, (ii) ascomycetes and (iii) basidiomycetes.

Thus, the fungicidal compositions, compounds and plant extracts of the present invention are used to control plant fungal pathogens. In a preferred embodiment, said plant fungal pathogen is selected from (i) oomycetes, (ii) ascomycetes and (iii) basidiomycetes.

Typically and preferably, said (i) oomycetes are selected from the order of Peronosporales, in particular the genera *Hyaloperonospora*, *Peronospora*, *Plasmopara*, *Bremia*, *Pseudoperonospora* and *Phytophthora*; in particular the species *Hyaloperonospora brassicae* (downy mildew of several Brassicacea), *Plasmopara viticola* (grapevine downy mildew), *Plasmopara halstedii* and *Plasmopara helianthii* (sunflower downy mildew), *Pseudoperonospora cubensis* (cucurbit downy mildew) and *Pseudoperonospora humuli* (downy mildew of hops), *Bremia lactucae* (downy mildew of lettuce), *Peronospora tabacinae* (downy mildew of tobacco), *Peronospora* destructor (downy mildew of onion), *Peronospora manshurica* (downy mildew of soybean and soybean leaf spot), *Peronospora parasitica* (downy mildew of cabbage), *Peronospora farinosa* (downy mildew of chicory and beetroot), *Phytophthora phaseoli*, *Phytophthora citrophthora*, *Phytophthora capsici*, *Phytophthora drechsleri*, *Phytophthora nicotianea*, *Phytophthora cactorum*, *Phytophthora palmivora*, *Phytophthora cinnamoni*, *Phytophthora megasperma*, *Phytophthora parasitica*, *Phytophthora fragariae*, *Phytophthora cryptogea*, *Phytophthora porri*, *Phytophthora nicotianae*, *Phytophthora infestans* (downy mildew of Solanaceae, in particular late blight of potato or tomato), *Phytophthora ramorum*.

Typically and preferably, said (ii) ascomycetes are selected from the genus *Alternaria*, in particular *Alternaria solani* (early blight of Solanaceae and in particular of tomato and potato) or *Alternaria alternata*, the genus *Guignardia*, in particular *Guignardia bidwelli* (black rot of grapevine); the genus *Venturia*, in particular *Venturia inaequalis* (apple scab), *Venturia carpophila*, *Venturia cerasi*, *Venturia pyrina*, *Venturia pirina* (pear scabs); the genus *Oidium*, in particular powdery mildew of grapevine (*Oidium tuckerii* (synonyms *Uncinula necator*, *Erysiphe necator*); the genus *Erysiphe*, in particular *Erysiphe polygoni* (powdery mildew of Cruciferae), *Erysiphe cichoracearum* (powdery mildew of cucurbits, of composites and of tomato), *Erysiphe communis* (powdery mildew of beetroot and cabbage), *Erysiphe pisi* (powdery mildew of pea and lucerne), *Erysiphe polyphaga* (powdery mildew of haricot bean and cucumber), *Erysiphe umbelliferarum* (powdery mildew of Apiaceae, in particular of carrot), *Erysiphe graminis* (synonym *Blumeria graminis*, powdery mildew of wheat and barley); the genus *Sphaeroteca*, in particular *Sphaerotheca humuli* (hop powdery mildew), *Sphaerotheca fuligena*; the genus *Leveillula*, in particular *Leveillula taurica* (onion powdery mildew), the genus *Podosphaera*, in particular *Podosphaera leucotricha* (apple powdery mildew); the genus *Marssonina*, in particular *Marssonina coronaria* (synonym *Diplocarpon mali*); the genus *Taphrina*, in particular *Taphrina deformans* (peach leaf curl); the genus *Septoria*, in particular *Septoria nodorum* or *Septoria tritici* (*Septoria* disease of cereals), the genus *Sclerotinia*, in particular *Sclerotinia sclerotinium*; the genus *Pseudocercosporella*, in particular *Pseudocercosporella herpotrichoides* (eyespot of cereals); the genus *Botrytis*, in particular *Botrytis cinerea* (grapevine, vegetable and market garden crops, pea and the like); the genus *Phomopsis*, in particular *Phomopsis viticola* (excoriosis of grapevine); the genus *Pyrenospora*; the genus *Helminthosporium*, in particular *Helminthosporium tritici* repentis (yellow leaf spot of wheat) or *Helminthosporium teres* (yellow leaf spot of barley); or the genera *Drechslera* or *Pyrenophora*.

Typically and preferably, said (iii) basidiomycetes are selected from the genus *Puccinia*, in particular *Puccinia recondita* or *Puccinia striiformis* (wheat rust), *Puccinia triticina*, *Puccinia hordei*; the genus *Phacopsora*, in particular *Phacopsora pachyrhizi*; or the genus *Rhizoctonia*, in particular *Rhizoctonia solani*.

In a further preferred embodiment, said plant fungal pathogen is selected from (i) oomycetes, (ii) ascomycetes and (iii) basidiomycetes, and wherein said (i) oomycetes are selected from the genera *Hyaloperonospora*, *Peronospora*, *Plasmopara*, *Bremia*, *Pseudoperonospora* and *Phytophthora*; and wherein said (ii) ascomycetes are selected from the genera *Alternaria*, *Guignardia*, *Venturia*, *Oidium*, *Erysiphe*, *Sphaeroteca*, *Leveillula*, *Podosphaera*, *Marssonina*, *Taphrina*, *Septoria*, *Sclerotinia*, *Pseudocercosporella*, *Botrytis*, *Phomopsis*, *Pyrenospora*; *Helminthosporium*, *Drechslera* and *Pyrenophora*; and wherein said (iii) basidiomycetes are selected from the genera *Puccinia*, *Phacopsora*, and *Rhizoctonia*.

In a further very preferred embodiment, said plant fungal pathogen is selected from *P. viticola*, *V. inaequalis*, *P. infestans*, *M. coronaria* and *Oidium tuckeri*.

In a further embodiment, said use as a fungicide of the inventive compositions, compounds and plant extracts is for controlling a fungal infection of a plant, plant propagation material or soil, preferably of a plant or plant propagation material, and again further preferably of a plant. In a further embodiment, said fungal infection is a fungal infection of a crop or a forestry plant. In a further very embodiment, said fungal infection is a fungal infection of a crop. In a further very embodiment, said fungal infection is a fungal infection of a crop selected from a horticultural crop or a field crop. In a further very embodiment, said fungal infection is a fungal infection of a crop selected from a horticultural crop preferably of a fruit crop or a vegetable. In a further very embodiment, said fungal infection is a fungal infection of a horticultural crop. In a further very embodiment, said fungal infection is a fungal infection of a field crop. In a further very embodiment, said fungal infection is a fungal infection of a fruit crop. In a further very embodiment, said fungal infection is a fungal infection of a vegetable. In a further very preferred embodiment, said fungal infection is a fungal infection of a fruit crop selected from a grapevine plant or an apple tree. In a further very preferred embodiment, said fungal infection is a fungal infection of a vegetable, wherein said vegetable is a tomato plant.

In a further very preferred embodiment, said fungal infection is a fungal infection of a fruit crop or of a vegetable, wherein said fruit crop is a grapevine plant or an apple tree and said vegetable is a tomato plant. In a further very preferred embodiment, said fungal infection is a fungal infection of grapevine plant, apple trees or tomato plants.

In a further very preferred embodiment, said fungal infection is a fungal infection of a crop selected from a fruit crop or a vegetable, wherein preferably said fruit crop is a grapevine plant or an apple tree and wherein preferably said vegetable is a tomato plant.

In a very further preferred embodiment, the composition in accordance with the present invention is used for controlling a plant fungal pathogen and for controlling a fungal infection selected from (i) a fungal infection of grapevine with *P. viticola* (grapevine downy) and/or *Oidium tuckeri* (powdery mildew); (ii) a fungal infection of apple trees with *V. inaequalis* (apple scab) and/or *Diplocarpon mali/Marssonina coronaria* (*Marssonina* leaf drop); or (iii) a fungal infection of tomato plants with *P. infestans* (tomato late blight).

A further preferred embodiment includes the instance where the plant infected with said plant fungal pathogen is selected from a grapevine plant, an apple tree and a tomato plant.

In a further embodiment, said composition further comprises an agriculturally acceptable excipient. Typically and preferably the inventive composition comprises one or more agriculturally acceptable excipients. The term "agriculturally acceptable excipient" as used herein refers to an excipient that is not unacceptably damaging to a plant or its environment, and/or not unsafe to the user or others that may be exposed to the material when used as described herein. In a preferred embodiment, said agriculturally acceptable excipient may comprise a liquid or solid carrier, surface-active agents, crystallisation inhibitors, viscosity-modifying substances, dyes, anti-oxidants, foaming agents, light absorbers, mixing aids, antifoams, complexing agents, neutralising or pH-modifying substances and buffers, thickeners, anti-freezes, microbiocides, stabilizers, and also liquid and solid fertilisers. The compositions according to the invention can additionally include an efficacy-enhancing additive commonly referred to as an adjuvant.

In a further very preferred embodiment, said controlling said plant fungal pathogen or said controlling said fungal infection of said plant, plant propagation material or soil, comprises applying an effective amount of said composition to said plant, plant propagation material or soil, preferably to said plant or plant propagation material, and further preferably to said plant, wherein preferably said effective amount of said composition applied to said plant, plant propagation material or soil, preferably to said plant or plant propagation material, and further preferably to said plant, is an amount of said composition sufficient to provide a concentration of said at least one compound of formula (I) or formula (II) of 0.02% or a concentration of 0.02%, of the sum of all of said at least one compound of formula (I) and formula (II), or to provide a concentration of said at least one plant extract, preferably said extract of a resin of said plant, of 0.05%.

In a further preferred embodiment, said plant extract is an extract of a resin of said plant, and wherein the concentration of said resin in said extract is from 0.1 g l$^{-1}$ to 100 g l$^{-1}$, preferably wherein the concentration of said resin in said extract is from 1 g l$^{-1}$ to 10 g l$^{-1}$.

The compounds, plant extracts and compositions according to the invention can be used as fungicides in unmodified form. Typically and preferably, said compounds, plant extracts and said compositions according to the invention will be further converted to formulations, such as wettable powders, water-dispersible granules, emulsifiable granules, emulsifiable concentrates, microemulsion concentrates, oil-in-water (EW) or water-in-oil (WO) emulsions, suspoemulsions, capsule suspensions or other formulations as, for example, defined in the Manual on Development and Use of FAO Specifications for Plant Protection Products, March 2006 revision of the First edition. Such formulations can either be used directly or are diluted prior to use. Dilution media for the formulations can be, for example, water, liquid fertilisers, oils or solvents. Water is generally the preferred carrier for the dilution of the formulations. The formulations can be applied as such or in diluted form through suitable ground spray equipment or through aerial application known to the person skilled in the art.

Thus, in a further very preferred embodiment, said composition is adapted as a formulation, wherein preferably said formulation is selected from a wettable powder, an emulsifiable concentrate, a water-dispersible granule, an emulsifiable granule, a microemulsion concentrate, an oil-in-water (EW) or water-in-oil (WO) emulsion, a suspo-emulsion and a capsule suspension. In a further very preferred embodiment, said composition is adapted as a formulation, wherein said formulation is selected from a wettable powder, an emulsifiable concentrate, a water-dispersible granule or an emulsifiable granule.

The formulations are produced in a manner known for the person skilled in the art, for example by mixing the compounds, plant extracts and compositions according to the invention with formulation adjuvants in order to obtain compositions in the form of finely divided solids, granules, solutions, dispersions or emulsions. The compounds, plant extracts and compositions according to the invention can also be contained in fine microcapsules consisting of a core and a polymeric shell. The formulation adjuvants suitable for the preparation of the compositions according to the invention are known to those skilled in the art.

Liquid carriers which may be used are, for example, water or organic solvents. Organic solvents comprise aromatic solvents such as toluene, xylene, aromatic hydrocarbon blends with boiling ranges between 150 and 300° C. known under various trademarks like AROMATIC®, SOLVESSO®, SHELLSOL A®, CAROMAX®, HYDROSOL®; paraffinic and isoparaffinic hydrocarbon solvents with boiling ranges between 150 and 360° C. known for example under the trademarks EXXSOL®, VARSOL®, ISOPAR® or SHELLSOL T®; hydrocarbons such as cyclohexane, tetrahydronaphthalene (tetralin), decahydronaphthalene, alpha-pinene, d-limonene; ester solvents such as ethyl acetate, n/iso-butyl acetate, amyl acetate, isobornyl acetate; alkyl esters of lactic acid; alkyl and aryl esters of benzoic acid such as methyl benzoate, benzyl benzoate, dipropyleneglycol dibenzoate; polar solvents like N-methyl pyrrolidone, N-ethyl pyrrolidone, $C_3$-$C_{18}$-alkyl pyrrolidones, dimethylsulfoxide, gamma-butyrolactone, N,N-dimethylformamide, N,N-dimethylacetamide, N,N-dimethyllactamide, $C_4$-$C_{18}$ fatty acid dimethylamides, benzoic acid dimethylamide, methyl-isobutyl ketone, isoamyl ketone, 2-heptanone, cyclohexanone, isophorone, mesityl oxide, acetophenone, ethylene carbonate, propylene carbonate, butylene carbonate; alcoholic solvents and diluents such as methanol, ethanol, propanol, n/iso-butanol, n/iso-pentanol, 2-ethyl hexanol, n-octanol, tetrahydrofurfuryl alcohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents, polyethylene glycol (PEG 400), glycerol, glycerol acetate, glycerol diacetate, glycerol triacetate; fatty acid esters such as methyl octanoate, isopropyl myristate, methyl laurate, methyl oleate, mixture of C8-C10 fatty acid methyl esters, rape seed oil methyl and ethyl esters, soy bean oil methyl and ethyl esters, vegetable oils; fatty acids such as oleic acid, linoleic acid, linolenic acid; phosphate and phosphonate esters such as triethyl phosphate, C3-C18-alkyl phosphates, alkyl-aryl phosphates, esters of alkylphosphonic acid.

Suitable solid carriers are, for example, ground natural minerals such as kaolins, clays, attapulgite clay, precipitated or fumed silica, talc, titanium dioxide diatomaceous earth, limestone, calcium carbonate, bentonite or ground organic materials such as sawdust, coconut shells, maize cobs, cottonseed husks, wheatmeal, soybean flour, ground walnut shells, lignin and similar materials.

A large number of surface-active substances can be used both in solid and in liquid formulations. Surface-active substances may be anionic, cationic, amphoteric, non-ionic or polymeric and they may be used as emulsifiying, wetting, dispersing or suspending agents or for other purposes. Typical surface-active substances include, for example, salts of alkyl sulfates, such as sodium lauryl sulphate; salts of alkylaryl sulfonates, such as calcium or sodium dodecylbenzene sulfonate; salts of alkylnaphthalene sulfonates, such as sodium dibutylnaphthalene sulfonate; dialkyl esters of sulfosuccinate salts, such as sodium di(2-ethylhexyl)sulfosuccinate; sodium salts of naphthalene sulfonic acid; formaldehyde condensation products; calcium or sodium ligninsulfonates; ethoxylated castor oils with 10-40 mol % ethylene oxide; alkylphenol-alkylene oxide addition products, such as nonylphenol ethoxylates; alcohol-alkylene oxide addition products, such as tridecyl alcohol ethoxylates; soaps, such as sodium stearate; sorbitol esters, such as sorbitol oleate; polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can be used in the compositions of the invention include crystallisation inhibitors, viscosity-modifying substances, dyes, anti-oxidants, foaming agents, light absorbers, mixing aids, antifoams, complexing agents, neutralising or pH-modifying substances and buffers, thickeners, anti-freezes, microbiocides, stabilizers, and also liquid and solid fertilisers. The compositions according to the invention can additionally include an efficacy-enhancing additive commonly referred to as an adjuvant. Examples of such adjuvants are oils of vegetable or animal origin, alkyl esters of such oils or mixtures of such oils and oil derivatives, or mineral oils. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid and mixtures thereof. The application and action of the oil additives can be further improved by combining them with surface-active substances, such as non-ionic, anionic, cationic or amphoteric surfactants. A preferred anionic surfactant is the calcium salt of dodecylbenzene sulfonic acid. Preferred non-ionic surfactants are ethoxylates of fatty alcohols. Special preference is given to ethoxylated $C_{12}$-$C_{22}$ fatty alcohols having a degree of ethoxylation of from 5 to 40%. Also preferred are silicone surfactants, especially polyalkyl-oxide-modified heptamethyltrisiloxanes, which are commercially available e.g. as Silwet L-77®. The concentration of surface-active substances in relation to the total additive is generally from 1 to 30% by weight. The said surface-active substances may also be used as efficacy enhancing additives alone without oil. The oil additive can be added to the spray tank in the desired concentration after the spray mixture has been prepared or built-in into the formulation.

The fungicidal compositions according to the invention generally comprise between 0.1 and 95% by weight of fungicidal compounds or plant extracts and preferably between 0.5 and 90%, more preferably from 5 to 99.9% by weight of a formulation adjuvant.

In a further aspect, the present invention provides for the use of a composition as a fungicide, wherein said composition comprises at least one plant extract, wherein said at least one plant extract is an extract from a plant of the family of Styracaceae or a plant of the genus *Myroxylon*. In a preferred embodiment of said use, said at least one plant extract is an extract from the genus *Styrax* or a plant of the genus *Myroxylon*. In a very preferred embodiment, said at least one plant extract is an extract of *Styrax tonkinensis, Styrax benzoin, Styrax paralleloneurum* or *Myroxylon balsamum*, and wherein preferably said at least one plant extract is an extract of a resin of Siam benzoin or Sumatra benzoin or Balsam of Peru. In a further preferred embodiment, said at least one plant extract is an extract from a plant of the genus *Styrax*, and wherein preferably said plant of the genus *Styrax* is selected from the species *Styrax tonkinensis, Styrax benzoin, Styrax paralleloneurum, Styrax hypoglauca* and *Styrax cascarifolia* or a subspecies or variety thereof, and wherein further preferably said plant of the genus *Styrax* is selected from the species *Styrax tonkinensis, Styrax benzoin* and *Styrax paralleloneurum* or a subspecies or variety thereof. In a further preferred embodiment, said at least one plant extract is an extract from a plant of the genus *Styrax*, and wherein said plant of the genus *Styrax* is from the species *Styrax tonkinensis* or a subspecies or variety thereof, and wherein further preferably said plant of the genus *Styrax* is selected the species *Styrax tonkinensis*. In a further preferred embodiment, said at least one plant extract is an extract from a plant of the genus *Styrax*, and wherein said plant of the genus *Styrax* is selected from the species *Styrax benzoin, Styrax paralleloneurum* or a subspecies or variety thereof, and wherein further preferably said plant of the genus *Styrax* is selected from the species *Styrax benzoin* and *Styrax paralleloneurum*. In a further preferred embodiment, said at least one plant extract is an extract from a plant of the genus *Myroxylon*, and wherein preferably said plant of the genus *Myroxylon* is selected from the species *Myroxylon balsamum* and *Myroxylon peruiferum*. In again a further preferred embodiment, wherein said plant of the genus *Styrax* is selected from the species *Styrax tonkinensis, Styrax benzoin, Styrax paralleloneurum, Styrax hypoglauca* and *Styrax cascarifolia* or a subspecies or variety thereof, and wherein said plant of the genus *Myroxylon* is selected from the species *Myroxylon balsamum* and *Myroxylon peruiferum*. In again a further preferred embodiment, said at least one plant extract is an extract of *Styrax tonkinensis, Styrax benzoin, Styrax paralleloneurum* or *Myroxylon balsamum*, and wherein preferably said at least one plant extract is an extract of a resin of Siam benzoin or Sumatra benzoin or Balsam of Peru. In a very preferred embodiment, said composition comprises at least one plant extract, wherein said at least one plant extract is an extract of *Styrax tonkinensis, Styrax benzoin, Styrax paralleloneurum* or *Myroxylon balsamum*, and wherein preferably said at least one plant extract is an extract of a resin of Siam benzoin or Sumatra benzoin or Balsam of Peru. In a very preferred embodiment, said composition comprises at least one plant extract, wherein said at least one plant extract is an extract of *Styrax tonkinensis*, and wherein said at least one plant extract is an extract of a resin of Siam benzoin. In a very preferred embodiment, said composition comprises at least one plant extract, wherein said at least one plant extract is an extract of *Styrax benzoin* or *Styrax paralleloneurum*, and wherein said at least one plant extract is an extract of a resin of Sumatra benzoin. In a very preferred embodiment, said composition comprises at least one plant extract, wherein said at least one plant extract is an extract of *Myroxylon balsamum*, and wherein said at least one plant extract is an extract of a resin of Balsam of Peru.

In again a further aspect, the present invention provides for the use of a composition as a fungicide, wherein said composition comprises an extract of Sumatra benzoin, Siam benzoin and Balsam of Peru. In again a further aspect, the present invention provides for the use of a composition as a fungicide, wherein said composition comprises an extract of Sumatra benzoin. In again a further aspect, the present invention provides for the use of a composition as a fungicide, wherein said composition comprises an extract of Sumatra benzoin. In again a further aspect, the present invention provides for the use of a composition as a fungicide, wherein said composition comprises an extract of Balsam of Peru.

EXAMPLES

Various aspects of the invention make use of the following materials and methods and are illustrated by the following non-limiting examples.

Materials and Methods

Phytochemistry

1. Chemicals:

Solvents and formic acid were obtained from Scharlau (Barcelona, Spain). For extraction, technical grade solvents were used after redistillation. For high-performance liquid chromatography (HPLC), HPLC-grade solvents were used. HPLC grade water was obtained from a MilliQ water purification system (Merck Millipore, Darmstadt, Germany). Deuterated solvents for NMR analysis were purchased from ARMAR Chemicals (Dottingen, Switzerland).

2. Plant Material:

Siam benzoin, further referred to as "SB" and Sumatra benzoin (below referred to as "SumB") were purchased from Alfred Galke GmbH (Gittelde, Germany). The plant material was imported from Laos (SB) or Java, Indonesia (SumB), respectively. Balsam of Peru (below referred to as "BP") was purchased from Hänseler AG (Herisau, Switzerland). Voucher specimens (Nr. 900, SB; Nr. 959, SumB, Nr. 988, BP) are kept at the Division of Pharmaceutical Biology, University of Basel, Switzerland.

3. General Procedures:

Preparative HPLC of Siam benzoin was performed on a LC8A Preparative Liquid Chromatograph consisting of a SCL-10VP controller, LC-8A binary pumps, and a UV-vis SPD-M10A detector (Shimadzu, Kyoto, Japan), using a SunFire™ Prep $C_{18}$ OBD column (5 µm, 150×30 mm i.d., Waters, Milford, Mass., USA). For Sumatra benzoin and balsam of Peru, preparative HPLC was carried out on a PURIFLASH® 4100-250 system (Interchim, Montluçon, France) equipped with a SUNFIRE™ Prep C18 OBD column (5 µm, 150×30 mm i.d., Waters, Milford, Mass., USA). Semi-preparative HPLC was performed on an Agilent 1100 Series with a PDA detector (Santa Clara, Calif., USA) connected to a FC204 fraction collector (Gilson, Middleton, Wis., USA). Separations were carried out on a SUNFIRE™ Prep C18 column (5 µm, 150×10 mm i.d., Waters) equipped with a guard column (10×10 mm i.d.). NMR spectra were recorded on a 500 MHz AVANCE III™ spectrometer (Bruker Biospin, Rheinstetten, Germany) equipped with a 1 mm TXI microprobe. Standard pulse sequences of the software package Topspin 3.0 were used.

4. Extraction:

For the preparation of a petroleum ether extract of Siam benzoin the resin was frozen with liquid nitrogen and milled with an Universal Mill M20 (IKA®-Werke, Staufen im Breisgau, Germany). The powdered material (9 kg) was separated in two portions of about 4.5 kg, then mixed with sea sand and rough sand (1:2). Each portion was then filled in a column and percolated during 4 days with about 45 L of petroleum ether. After evaporation under reduced pressure, 340 g of extract were obtained (yield: 3.8%). The petroleum ether extract is referred herein as "SB-PE" or "SumB-PE". Alternatively, Siam benzoin and Sumatra benzoin were dissolved directly in ethanol (250 g $l^{-1}$). Both resins are fully soluble in EtOH with exception of some pieces of bark trapped in the resin. Balsam of Peru was dissolved in ethanol (250 g$l^{-1}$). These ethanol extracts are referred herein as "SB-EtOH", "SumB-EtOH", or "BP-EtOH".

5. HPLC Microfractionation:

Microfractionation was performed by semi-preparative HPLC. The mobile phase consisted of water with 0.1% formic acid (Solvent A) and acetonitrile containing 0.1% formic acid (Solvent B). A gradient of 5 to 100% B in 30 min was used, followed by isocratic conditions of 100% B for 5 min. The flow rate was 4.0 ml min$^{-1}$. The extract was dissolved in DMSO at a concentration of 50 mg ml$^{-1}$, centrifuged, and filtered. Two injections of 200 µL were performed (20 mg of extract in total). Microfractions were collected every 90 sec from 1 to 34 min (22 fractions per injection). After removal of the eluent in a Genevac EZ-2 evaporator (Stone Ridge, N.Y., USA), the fractions were re-dissolved in 300 µL of methanol. The corresponding fractions obtained from the two separations were combined and re-dried. Before testing in in vitro bioassays, the fractions were re-dissolved in 70 µL DMSO.

6. Isolation of the Active Constituents:

6.1. Coniferyl Benzoate:

A portion (600 mg) of Siam benzoin petroleum ether extract was separated by preparative HPLC in 6 aliquots dissolved in DMSO to afford pure coniferyl benzoate (192 mg, $t_R$=10.7 min). The sample was dissolved immediately prior each injection. The mobile phase consisted of water with 0.1% formic acid (Solvent A) and acetonitrile with 0.1% formic acid (Solvent B). Isocratic elution with 60% B was used. The flow rate was 20 ml min$^{-1}$. Purity of coniferyl benzoate was ≥98% as determined by $^1$HNMR analysis.

6.2. Coumaryl Cinnamate:

Separation of Sumatra benzoin (6×100 mg dissolved in DMSO) by preparative HPLC afforded pure coumaryl cinnamate (135 mg, $t_R$=16.5 min). The mobile phase consisted of water with 0.1% formic acid (Solvent A) and acetonitrile with 0.1% formic acid (Solvent B). Isocratic elution with 60% B was used. The flow rate was 20 ml min$^{-1}$. Purity of coumaryl cinnamate was ≥98% as determined by $^1$HNMR analysis.

6.3 Benzyl Cinnamate:

Separation of Balsam of Peru (270 mg) by preparative HPLC in 4 aliquots provided pure benzyl cinnamate ($t_R$=19.3 min, 55 mg). The mobile phase consisted of water (solvent A) and acetonitrile (solvent B). Isocratic elution with 50% B for 2 min, followed by a gradient of 50 to 100% B in 20 min was applied. The flow rate was 20 ml min$^{-1}$. Purity was ≥95% as determined by $^1$HNMR analysis.

7. Quantification of the Active Constituents:

7.1.: Coniferyl Benzoate:

Analyses were performed in triplicate on a HPLC Alliance 2695 chromatographic system (Waters) equipped with a 996 PDA detector. Separation were carried out on a SunFire $C_{18}$ (3.5 µm, 150×3.0 mm i.d., Waters) column equipped with a guard column (10 mm×3.0 mm i.d.). The mobile phase consisted of water with 0.1% formic acid (Solvent A) and acetonitrile with 0.1% formic acid (Solvent B). The flow rate was 0.4 ml min$^{-1}$. A gradient of 50 to 100% B in 30 min, followed by isocratic conditions of 100% B for 5 min was used. Samples were dissolved in acetonitrile at a concentration of 100 µg ml$^{-1}$ for the extract and 25-125 µg ml$^{-1}$ for coniferyl benzoate. The autosampler temperature was set at 4° C. The injection volume was 10 µl. Detection was at 267 nm. A calibration curve was used to determine the concentration of coniferyl benzoate in the extract: 84047x+ 399888 ($r^2$=0.9965).

7.2.: Coumaryl Cinnamate:

Analyses were performed in triplicate on a Binary Gradient prominence LCMS/MS 8030 system (Shimadzu) equipped with a PDA detector. Separation were carried out on a SunFire™ $C_{18}$ (3.5 µm, 150×3.0 mm i.d.) column equipped with a guard column (10 mm×3.0 mm i.d.). The mobile phase consisted of water with 0.1% formic acid (Solvent A) and acetonitrile with 0.1% formic acid (Solvent B). The flow rate was 0.4 ml min$^{-1}$. A gradient of 30 to 70% B in 30 min, followed by isocratic conditions of 100% B for 5 min was used. Samples were dissolved in ethanol at a concentration of 100 µg ml$^{-1}$ for the extract and 25-125 µg ml$^{-1}$ in acetonitrile for coumaryl cinnamate. The autosampler temperature was set at 4° C. The injection volume was 10 µl. Detection was at 272 nm. A calibration curve was used to determine the concentration of coumaryl cinnamate in the extract: 182702x −57264 ($r^2$=0.9999).

Formulation

For field trials, Siam benzoin petroleum ether extract or Siam benzoin were used in formulations to improve handling, application and properties in the field (e.g. rain fastness). For field trials 2014, the extract was dissolved in a solvent, stabilized and water-diluted before use. For field trials 2015, Siam benzoin was tested as a wettable powder (SB WP; 20% (w/w) Siam benzoin) and an emulsifiable concentrate (SB EC, 15% Siam benzoin resin (w/w)) formulation. A plant oil sticker was added to the spray broth at a final concentration of 0.3%. Blank formulations were tested in semi-controlled bioassays with no or minor effects on the studied plant diseases (data not shown).

Bioassays

1. Pathogens:

*Phytophthora infestans* (Mont.) de Bary was cultivated on V8 agar (200 ml l$^{-1}$ Campbell's V8 or "BIOTTA® Gemüsecocktail" (vegetable juice) (Biotta AG, Tagerwilen, Switzerland), 3 g l$^{-1}$ CaCO$_3$, 1.5% Agar, pH 6.3) at 20° C. in the dark. *Venturia inaequalis* Cooke (Wint.) and *Marssonina coronaria* (Ell. et J. J. Davis) were maintained on apple (*Malus domestica* Borkh.) seedlings cv. 'Jonagold' as described below. Leaves with sporulating lesions were dried at room temperature before storing them in glass vessels at 4° C. in the dark. *Plasmopara viticola* (Berk. & M. A. Curtis) Berl. & De Toni was maintained on grapevine (*Vitis vinifera* L.) seedlings cv. 'Chasselas' by weekly re-inoculation (described below).

2. In Vitro Bioassays:

2.1. General Procedures:

All in vitro experiments were performed in 96-well plates. Media appropriate for each pathogen were used, namely mineral water ('Evian') for *P. viticola*, demineralised water for *V. inaequalis*, and demineralized water containing 1 ml l$^{-1}$ V8-medium (200 ml l$^{-1}$ Campbell's V8, 3 g CaCO$_3$, pH 6.3) for *P. infestans*. Each test plate contained at least 16 non-treated control wells. The effect of the solvent (DMSO) alone was tested in at least eight replicates in three concentrations per experimental set.

Sporangia suspensions of *P. viticola* (1.8-2.5×10$^5$ sporangia ml$^{-1}$) and conidia suspensions of *V. inaequalis* (1.5-2.0× 10$^5$ conidia ml$^{-1}$) were prepared by washing fresh (*P. viticola*) or dry (*V. inaequalis*) sporulating leaves with demineralized water. Sporangia suspensions of *P. infestans* (1.2-1.5×10$^5$ sporangia ml$^{-1}$) were prepared by placing mycelium dispatched from 10-14 d old cultures into demineralized water and shaking vigorously. Suspensions were filtered over a cheese cloth, the concentration was assessed using a Thoma cell counting chamber, and adjusted to desired concentrations.

2.2. Profiling of Microfractions:

To determine activity of microfractions against *P. viticola, V. inaequalis, P. infestans*, 6 ul of the test product were added to 96-well plates containing 94 ul of the medium appropriate for each pathogen. Extracts were then serially diluted in the test plate 1:10 and 1:100 by adding 10 ul of the next higher concentration to 90 ul of the appropriate test medium, the 10 ul of the lowest concentration being discarded. Then, 20 ul of a continuously stirred pathogen suspension were added to each well, resulting in extract concentrations of 490, 49 and 4.9 ug ml$^{-1}$.

2.3. Determination of Minimal Inhibitory Concentrations (MIC$_{100}$):

To determine the concentrations needed to completely inhibit germination of spores or activity of zoospores (MIC$_{100}$), test products (Siam benzoin petroleum ether extract, Siam benzoin, Sumatra benzoin, coniferyl benzoate or p-coumaryl cinnamate) were dissolved either in DMSO or EtOH (98.9%) at concentrations of 10 mg ml$^{-1}$. Then, they were serially diluted 1:1 in water down to 0.02 mg ml$^{-1}$ (10 concentrations). 6 ul of each test product and dilution were added to a well containing 94 ul of the appropriate medium before adding 20 ul of pathogen suspension.

2.4 Assessment of Inhibitory Activity:

Effects of extracts were assessed 2-3 h (*P. viticola*), one day (*P. infestans*, bacteria), or two days (*V. inaequalis*) after set-up of the experiment. All assessments were made using a binocular at magnifications×50 to 100. Inhibition levels were scored according to Table 1.

TABLE 1

Assessment of inhibition levels caused by plant extracts against *Phytophthora infestans, Venturia inaequalis* and *Plasmopara viticola* in in vitro experiments.

| Inhibition level | *P. infestans, V. inaequalis* | *P. viticola* |
|---|---|---|
| 0 | Similar to water control | Similar to water control |
| 1 | distinct reduction in germination rate and/or length of germ tubes | distinct reduction in number and/or activity of zoospores |

TABLE 1-continued

Assessment of inhibition levels caused by plant extracts against Phytophthora infestans, Venturia inaequalis and Plasmopara viticola in in vitro experiments.

| Inhibition level | P. infestans, V. inaequalis | P. viticola |
|---|---|---|
| 2 | no germination, or germ tubes ≤0.5* length of the sporangium/conidium | no zoospores germinated, or all zoospores inactive |

3. Plant-Pathogen Bioassays Under Semi-Controlled Conditions:

Plant-pathogen bioassays were carried out under semi-controlled conditions in experimental facilities (greenhouse and growth chambers). Small grapevine (cv. 'Chasselas'), apple (cv. 'Jonagold') or tomato (cv. 'Marmande') seedlings were transplanted to individual pots (0.275 l) containing a standard substrate ('Einheitserde Typ 0', Gebr. Patzer GmbH & Co. KG, Sinntal-Jossa, Germany) previously amended with 3 g l$^{-1}$ of a mineral fertilizer (Tardit 3M, Hauert Günther Düngerwerke GmbH, Erlangen, Germany). Plants were grown in the greenhouse at a temperature of 18 to 28° C. under natural light. In wintertime, the photoperiod was extended with mercury lamps to 16 hours. Plants were used for bioassays when they had 2-3 (P. infestans), 3-4 (P. viticola, V. inaeaualis) or 4-5 fully developed leaves (M. coronaria).

Each experimental set included a non-treated non-inoculated control, a water-treated inoculated control, a standard treatment (copper hydroxide, Kocide Opti, DuPont de Nemours, Wilmington, Del., USA) at two concentrations (0.3 g l$^{-1}$ and 0.03 g l$^{-1}$ of Cu$^{2+}$) (P. viticola, V. inaequalis, P. infestans) or two standard treatments (Bordeaux mixture, Bouille bordelaise RSR, Cerexagri S. A., Plaisir, France; 0.6 mg ml-1 Cu$^{2+}$); Limesulphur, Curatio, Biofa AG, Münsingen, Germany; 6 mg ml$^{-1}$) coronaria), and at least 12 test treatments. All experiments included six replicate plants per treatment. Test products were typically dissolved in DMSO, isopropylidenglycerol or EtOH at concentrations of 50 or 100 mg ml$^{-1}$ and then diluted into water to concentrations between 2 and 0.1 mg ml$^{-1}$.

Plants were sprayed with the test products using an air-assisted hand sprayer (DEVILBISS® Compact MINI HVLP Touch-Up Spray Gun) or an automatic spray cabinet until leaves (adaxial and abaxial side) were completely covered with a dense layer of small droplets. Plants were subsequently left to dry at room temperature before inoculation.

P. viticola, V. inaequalis and M. coronaria inocula were prepared from previously infected plants by washing freshly sporulating grapevine leaves, dried, infected apple leaves (V. inaequalis) or dry apple leaves with acervuli (M. coronaria) with water and filtering through cheese cloth. P. infestans inoculum was prepared from 10-12 d old cultures grown on V8-agar as described above. Concentration of the sporangia/conidia suspensions were adjusted to 5×10$^5$ sporangia ml$^{-1}$ (P. viticola), 7×10$^5$ conidia ml$^{-1}$ (V. inaequalis), 1.5-2×10$^5$ sporangia ml$^{-1}$ (M. coronaria) or 5×10$^4$ sporangia ml$^{-1}$ (P. infestans), respectively. Plants were spray-innoculated using an air-assisted hand sprayer on the abaxial (P. viticola) or the adaxial (V. inaequalis, M. coronaria, P. infestans) leaf side. Inoculated plants were subsequently incubated at 20-21° C. and 80-99% of relative humidity (RH) in the light for 24 h (P. viticola, V. inaequalis, P. infestans) or for a minimum of 72 h with a 16/8-h day/night light regime (M. coronaria).

Then, plants were maintained at 20° C., 60-80% RH, and a 16/8-h day/night light regime. For grapevine bioassays, 5 to 6 d after inoculation, plants were incubated over night in the dark at 20° C. and 80-99% to promote sporulation. Disease incidence (percentage of leaves with disease symptoms) and disease severity (percentage of leaf area covered by lesions) were assessed 5 d (P. infestans) 6 to 7 d (P. viticola), 10 to 12 d (V. inaequalis) or 14 d (M. coronaria) after inoculation. Disease assessments for all pathogens except M. coronaria were made using continuous values of percentage based on the EPPO standard scale. For M. coronaria, disease severity of each individual leaf was categorized into one of five classes (0: no disease symptoms, 1: 1-5 spots per leaf; 2: 6-20 spots per leaf; 3: 21-50 spots per leaf; 4: >50 spots per leaf) 14 d after inoculation. The relative frequency of each disease class was calculated per plant.

Field Trials

1. General Procedures:

Efficacy of Siam benzoin against downy mildew (Plasmopara viticola) and powdery mildew (Oidium tuckeri) was tested under field conditions (natural infections, no artificial inoculation). The experiments were conducted following EPPO guidelines (PP1/031(1) Plasmopara viticola; PP1/152 (4) Design and Analyses of Efficacy Trials; PP1/181(4) Conduct and Reporting of Efficacy Trials-GEP; PP1/135(3) Phytotoxicity assessment) (ppl.eppo.int/list.php). In 2015, experiments were performed under GEP.

2. Experimental Vineyard:

The experiment was carried out in the screening-vineyard of the Research Institute of Organic Agriculture in Frick, Switzerland, at 385 meters a.s.l, on a clayey loam. The coordinates of the experimental plot are: 47°31'4" N 08°01'33" E. Average annual rainfall is 1138 mm (mean 2005-2014, www.agrometeo.ch). The experimental vineyard was established in 1997 and consists of 576 plants of the susceptible grapevine varieties 'Muller-Thurgau' ('Riesling×Sylvaner') and 'Chasselas' ('Gutedel') (288 plants per variety). Plant distance between rows is 2 m, within rows 1.1 m (4545 plants/ha). The experiment was set up in a complete randomized block design, with twelve treatments arranged in 4 replicates of 6 plants for both grapevine varieties. Due to the age of the vineyard and its previous use in trials there are some plants of low quality. This resulted in some replicates having less than 12 plants. The vineyard was maintained according to guidelines for organic agriculture. Maintenance work included fertilization with an organic fertilizer and budding treatment with sulphur against mites in April, thinning of shoots, shortening of main and secondary shoots and grape zone defoliation.

Weather data were recorded throughout the season with a Campbell weather station close to the vineyard (www.agrometeo.ch).

3. Test Products:

As a copper control, Kocide Opti (copper hydroxide, DuPont de Nemours, Wilmington, Del., USA) was used at a final concentration of 0.1% of the product (containing 0.03% Cu$^{2+}$). 'Strategy Praxis' is the plant protection strategy recommended by the FiBL-advisory service to Swiss grapevine producers. The spray schedule starts with the use of 'Mycosin' (Andermatt Biocontrol, Grossdietwil, Switzerland; containing 65% acidified clay minerals, 0.2% horsetail extract, concentration of formulation 0.8%) plus 'Stulln Sulphur' (Andermatt Biocontrol, 80% sulphur, concentration of formulation 0.5%) in tank mixture. Around bloom, depending on infection pressure and rainfall, there is a change to copper (Kocide opti, 0.1%), which is sprayed until the end of the season. In 2014 and 2015, the change to copper was on 5 Jul. 2014 or 22 Jun. 2015 respectively, after 8 (2014) or 6 (2015) copper-free treatments. An untreated control serves as a reference for natural development of disease epidemic.

In 2014, Siam benzoin petroleum ether extract ("SB-PE") was tested at a concentration of 1 g l$^{-1}$. The extract was dissolved in a solvent before adding a stabilizer and dilution into water. In 2015, Siam benzoin was tested in two preliminary formulations, a wettable powder (SB WP) and an emulsifiable concentrate (SB EC). Both formulations were based on Siam benzoin and applied at a final concentration of 1 g l$^{-1}$ of the resin.

4. Applications:

Products were applied by hand using two pressure based and pressure tank supported spray systems (spray gun: GTi Pro light pressure, DeVillbiss, USA; pressure tank: pressure feed cup KB-522-SS, DeVillbiss, USA; 4 bar spray pressure). The two spray systems were calibrated to dispense similar amounts of product per unit of time.

Plants were treated by spraying the product from above and from below, which resulted in a homogeneous coating of the abaxial and adaxial leaf surface. Spray distribution was verified using water-sensitive paper (Novartis, Basel, Switzerland).

Plants were treated weekly or according to weather conditions and risk for infection, calculated by the forecast model 'vitimeteo' (www.agrometeo.ch). Treatments started 6 May (2014) or 13 May (2015) and ended on 20 (2014) or 21 (2015) August. In both years, a total of 16 treatments were performed in intervals of 3 to 10 days.

5. Disease Assessments 5.1 *Plasmopara viticola* (Downy Mildew):

Three (5, 19 and 27 Aug. 2014) or four (26 June, 3 July, 23 July, 18 Aug. 2015) disease assessments were carried out by scoring disease incidence (proportion of leaves with symptoms) and disease severity (proportion of diseased leaf area) of *Plasmopara viticola* (downy mildew) on leaves (assessment of 100 or all leaves per plant, all plants per variety and replication). In 2014, overall damage on grapes caused by downy and powdery mildew was assessed 9 Sep. 2014 for each treatment replicate. In 2015, percentage grape area infected by *P. viticola* was assessed 24 Jul. 2015 (assessment of all grapes per plant, all plants per variety and replication).

5.2 *Oidium tuckeri* (Powdery Mildew):

*Oidium tuckeri* on leaves was assessed once per season. In 2014, the percentage leaves with infections and the infected leaf area was assessed on 50 leaves per plant 11 Aug. 2014. In 2015, powdery mildew disease severity on leaves was categorized into four classes (0-3) (assessment of all leaves per plant, all plants per variety and replication) 21 Aug. 2015. In 2014, percentage grapes infected by powdery mildew was assessed 24 Jul. 2014 (assessment of all grapes per plant, all plants per variety and replication). In 2015, presence/absence of *O. tuckeri* on grapes was evaluated for each plant (24 Jul. 2015).

Calculations and Statistical Analyses

To calculate means and confidence intervals of $MIC_{100}$ values, data were log 2-transformed. 95% confidence intervals were calculated from transformed data as $A \pm 1.96*B*n^{-0.5}$, with A=mean $MIC_{100}$, B=standard deviation $MIC_{100}$ and n=number of experiments. Data were transformed back to the linear scale for presentation in tables.

To check for a treatment effect in field trials, a one-way analysis of variance and a comparison between the replicate means of all treatments was done by using Tukey's HSD (Honestly Significant Difference) test. Prior to all analysis, all data was arcsin-transformed (not shown).

Efficacies were calculated according to Abbott as $(1-(A*B^{-1}))*100$. In semi-controlled bioassays, A is disease severity/incidence on an individual plant and B mean disease severity/incidence of control plants. In field experiments, A is the mean disease severity/incidence of a treatment and B is the mean disease severity/incidence of the non-treated control.

Example 1

In Vitro Activity of Siam and Sumatra Benzoin and Identification of the Active Ingredients The petroleum ether extract of Siam benzoin ('SB-PE') showed strong activity against *Plasmopara viticola*, *Phytophthora infestans*, and *Venturia inaequalis* in in vitro bioassays, with minimal inhibitory concentrations ($MIC_{100}$) of 26 μg ml$^{-1}$ (*P. viticola*), 45 μg ml$^{-1}$ (*V. inaequalis*) and 32 μg ml$^{-1}$ (*P. infestans*) (Table 2). Similar results were found when Siam benzoin (SB) was directly dissolved in EtOH ("SB-EtOH") (Table 2). $MIC_{100}$ of Sumatra benzoin dissolved in EtOH ("SumB-EtOH") were between 48 μg ml$^{-1}$ (*P. viticola*) and 99 μg ml$^{-1}$ (*V. inaequalis*).

TABLE 2

Minimal inhibitory concentrations ($MIC_{100}$) of Siam benzoin petroleum ether extract (SB-PE), Siam benzoin (SB-EtOH), Sumatra benzoin (SumB-EtOH) dissolved in EtOH, coniferyl benzoate (CB) and p-coumaryl cinnamate (CC) against *Plasmopara viticola*, *Venturia inaequalis* and *Phytophthora infestans*. The table shows means (bold), lower and upper limits of the 95% confidence interval (in brackets) and number of independent experiments (N).

|  | P. viticola | | V. inaequalis | | P. infestans | |
|---|---|---|---|---|---|---|
|  | Mean[a] | N | Mean[a] | N | Mean[a] | N |
| SB-PE | 26 (13; 49)[b] | 8 | 45 (24; 78)[b] | 8 | 32 (8; 121)[b] | 3 |
| SB-EtOH | 14 (12; 18) | 2 | 63 (17; 240) | 2 | 32 (32; 32) | 2 |
| SumB-EtOH | 48 (32; 73) | 3 | 99 (46; 156) | 3 | 79 (32; 195) | 3 |
| CB | 12 (6; 22) | 7 | 35 (23; 54) | 7 | 21 (15; 29) | 5 |
| CC | 38 (27; 54) | 3 | 32 (15; 70) | 3 | 25 (16; 40) | 3 |

[a] μg ml$^{-1}$
[b] upper and lower limit of the 95% confidence interval in μg ml$^{-1}$ The active ingredient of Siam benzoin was identified by a process referred to as HPLC-based activity profiling. An aliquot of the petroleum ether extract was separated by semi-preparative HPLC and each fraction was tested in vitro against three plant pathogens. When the bioactivity data and the chromatographic trace were compared the activity could be mainly assigned to Fraction 14, eluting between 20.5 and 22.0 min (data not shown). This fraction contained a major peak which was isolated by preparative HPLC. It was identified by comprehensive NMR analysis as coniferyl benzoate (Compound 1). Coniferyl benzoate (CB) was subsequently quantified by HPLC-UV analysis and found to account for 43-53% of the petroleum ether extract, and 33-59% in the EtOH soluble part of the SB resin.

The HPLC chromatogram of Sumatra benzoin showed a major UV peak with a similar elution time as CB. After isolation, it was identified as p-coumaryl cinnamate (Compound 2), a chemically related ester. Quantitative analysis by HPLC-UV revealed that this compound made up 27-29% of SumB resin.

Minimal inhibitory concentrations $MIC_{100}$ of coniferyl benzoate against *P. viticola*, *V. inaequalis* and *P. infestans* ranged between 8 and 32 μg $ml^{-1}$ (Table 2). $MIC_{100}$ of p-coumaryl cinnamate (CC) were slightly higher, ranging between 16 and 64 μg $ml^{-1}$.

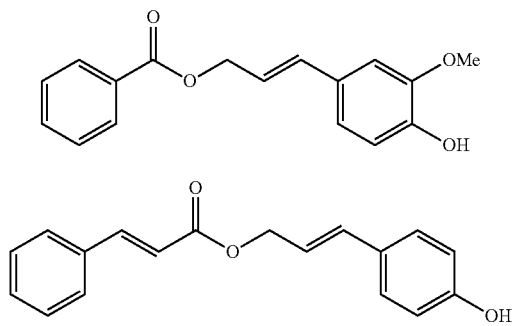

Example 2

Fungicidal Activity of Siam and Sumatra Benzoin and their Active Ingredients on Grapevine, Apple and Tomato Seedlings Under Semi-Controlled Conditions 2.1. Grapevine—*P. viticola*:

Efficacy of Siam benzoin petroleum ether extract on grapevine seedlings against *P. viticola* under semi-controlled conditions was very high. At an application rate of 1 mg $ml^{-1}$, the diseased leaf area was reduced by 99% compared to the non-treated control (i.e. 99% efficacy) in three out of four independent experiments and by 81% in a fourth experiment (Table 3). At 0.25 mg $ml^{-1}$, mean efficacy was still 75%. Efficacies of Siam benzoin and of Sumatra benzoin dissolved in EtOH (SB-EtOH, SumB-EtOH) were comparable (Table 4). Efficacies of purified coniferyl benzoate (CB) and p-coumaryl cinnamate (CC) were ≥98% at 1 mg $ml^{-1}$ and ≥80% at 0.25 mg $ml^{-1}$ (Table 5).

TABLE 3

Efficacy of Siam benzoin petroleum ether extract (SB-PE) (1 and 0.25 mg $ml^{-1}$) on grapevine seedlings against *P. viticola* under semi-controlled conditions, compared to efficacies of two concentrations of a copper reference treatment ($Cu^{2+}$ in the form of copper hydroxide, KOCIDE OPTI ®). The table shows results (means ± SD) of four (SB-PE 1 mg $ml^{-1}$) or two (0.25 mg $ml^{-1}$) independent experiments, each experiment with 6 replicate plants per treatment and concentration.

| | Efficacy (%) [1] | | | | Disease severity |
|---|---|---|---|---|---|
| | SB-PE | | $Cu^{2+}$ | | non-treated control |
| | Product Concentration (mg $ml^{-1}$) | | | | |
| | 1 | 0.25 | 0.3 | 0.03 | (%) [2] |
| Exp_1 | 81 ± 15 | | 100 ± 0 | 76 ± 17 | 65 ± 16 |
| Exp_2 | 99 ± 1 | 60 ± 9 | 99.6 ± 0.7 | 99.4 ± 0.5 | 77 ± 22 |

TABLE 3-continued

Efficacy of Siam benzoin petroleum ether extract (SB-PE) (1 and 0.25 mg $ml^{-1}$) on grapevine seedlings against *P. viticola* under semi-controlled conditions, compared to efficacies of two concentrations of a copper reference treatment ($Cu^{2+}$ in the form of copper hydroxide, KOCIDE OPTI ®). The table shows results (means ± SD) of four (SB-PE 1 mg $ml^{-1}$) or two (0.25 mg $ml^{-1}$) independent experiments, each experiment with 6 replicate plants per treatment and concentration.

| | Efficacy (%) [1] | | | | Disease severity |
|---|---|---|---|---|---|
| | SB-PE | | $Cu^{2+}$ | | non-treated control |
| | Product Concentration (mg $ml^{-1}$) | | | | |
| | 1 | 0.25 | 0.3 | 0.03 | (%) [2] |
| Exp_3 | 99 ± 1 | 90 ± 9 | 100 ± 0 | 95 ± 5 | 36 ± 18 |
| Exp_4 | 99 ± 1 | | 98 ± 2 | 89 ± 10 | 78 ± 5 |
| Mean [3] | 95 ± 9 | 75 ± 21 | 99 ± 1 | 90 ± 10 | 64 ± 20 |

[1] Percentage reduction in the diseased leaf area in treated plants compared to the non-treated control
[2] Percentage leaf area with disease symptoms;
[3] Mean and SD of all independent experiments

TABLE 4

Efficacy of Siam benzoin (SB-EtOH) and Sumatra benzoin (SumB-EtOH) dissolved in EtOH and a copper reference ($Cu^{2+}$ in the form of copper hydroxide, KOCIDE OPTI ®) against *Plasmopara viticola* on grapevine cv. 'Chasselas' seedlings under semi-controlled conditions. The table shows means ± SD (n = 6). Disease severity (percentage leaf area with disease symptoms) of the non-treated control was 82% ± 22%.

| Treatment | Concentration (mg $ml^{-1}$) | Efficacy Mean ± SD |
|---|---|---|
| $Cu^{2+}$ | 0.3 | 97 ± 2 |
| | 0.03 | 90 ± 7 |
| SB-EtOH | 2 | 98 ± 5 |
| | 1 | 100 ± 0 |
| | 0.5 | 92 ± 12 |
| | 0.25 | 87 ± 9 |
| | 0.125 | 41 ± 28 |
| SumB-EtOH | 2 | 99 ± 1 |
| | 1 | 100 ± 0 |
| | 0.5 | 96 ± 2 |
| | 0.25 | 92 ± 13 |
| | 0.125 | 81 ± 9 |

TABLE 5

Efficacy of coniferyl benzoate (CB) and p-coumaryl cinnamate (CC) against *P. viticola* on grapevine cv. 'Chasselas' seedlings under semi-controlled conditions. Each experimental set included a copper reference ($Cu^{2+}$ in the form of copper hydroxide, KOCIDE OPTI ®). The table show means ± SD (n = 6).

| Concentration | CB[1] | CC[2] |
|---|---|---|
| 1 mg ml$^{-1}$ | 99 ± 1 | 98 ± 1 |
| 0.5 mg ml$^{-1}$ | 77 ± 50 | 95 ± 6 |
| 0.25 mg ml$^{-1}$ | 85 ± 14 | 80 ± 16 |

[1] Disease severity control 49% ± 18%, efficacy $Cu^{2+}$ 100% ± 0% (0.3 gm ml$^{-1}$) and 99% ± 2% (0.03 mg mL$^{-1}$);
[2] Disease severity control 82% ± 22%, efficacy $Cu^{2+}$ 97% ± 2% (0.3 mg ml$^{-1}$) and 90 ± 7 (0.03 mg ml$^{-1}$)

2.2. Apple—*V. inaequalis*:

Efficacy of Siam benzoin petroleum ether extract on apple seedlings against *V. inaequalis* under semi-controlled conditions was between 95% and 99% at 2 mg ml$^{-1}$ and 83% and 95% at 1 mg ml$^{-1}$ (Table 6). Efficacy of coniferyl benzoate at 1 mg ml$^{-1}$ was 70% (Table 7).

TABLE 6

Efficacy of Siam benzoin petroleum ether extract (SB-PE) (1 and 2 mg ml$^{-1}$) on apple seedlings cv. 'Jonagold' against *V. inaequalis* under semi-controlled conditions, compared to efficacies of two concentrations of a copper reference treatment ($Cu^{2+}$ in the form of copper hydroxide, KOCIDE OPTI ®). The table shows results (means ± SD) of three independent experiments for each concentration of SB-PE, each experiment with 6 replicate plants per treatment and concentration.

| | Efficacy (%) [1] | | | | Disease severity non-treated control |
|---|---|---|---|---|---|
| | SB-PE | | $Cu^{2+}$ | | |
| | Product Concentration (mg ml$^{-1}$) | | | | |
| | 2 | 1 | 0.3 | 0.03 | (%) [2] |
| Exp_1 | | 83 ± 8 | 86 ± 12 | 62 ± 18 | 23 ± 14 |
| Exp_2 [4] | 99 ± 2 | 95 ± 3 | 87 ± 9 | 84 ± 15 | 28 ± 14 |
| Exp_3 [4] | 99 ± 2 | | 97 ± 2 | 87 ± 7 | 13 ± 4 |
| Exp_4 [4] | 95 ± 4 | 88 ± 8 | 92 ± 4 | 77 ± 18 | 33 ± 8 |
| Mean [3] | 98 ± 2 | 89 ± 6 | 91 ± 5 | 78 ± 11 | 24 ± 9 |

[1] Percentage reduction in the diseased leaf area in treated plants compared to the non-treated control;
[2] Percentage leaf area with disease symptoms;
[3] Mean and SD of all independent experiments,
[4] Siam benzoin petroleum ether extract in a formulation

TABLE 7

Efficacy of coniferyl benzoate (CB) and a copper reference ($Cu^{2+}$ in the form of copper hydroxide, KOCIDE OPTI ®) against *Venturia inaequalis* on apple cv. 'Jonagold' seedlings under semi-controlled conditions. The table shows means ± SD (n = 6). Disease severity (percentage leaf area with disease symptoms) of the non-treated control was 23% ± 14%.

| | Concentration | Efficacy Mean ± SD |
|---|---|---|
| CB | 1 mg ml$^{-1}$ | 69 ± 12 |
| | 0.1 mg ml$^{-1}$ | 4 ± 53 |
| $Cu^{2+}$ | 0.3 mg ml$^{-1}$ | 85 ± 12 |
| | 0.03 mg ml$^{-1}$ | 62 ± 18 |

Apple—*D. mali*

Siam benzoin significantly reduced *Marssonina* leaf drop caused by *M. coronaria* on apple seedlings compared to the non-treated control (Tab. 8). The percentage of leaves without any disease symptoms (disease category 0) or with few symptoms (category 1) was 83-98% in SB-treated plants compared to 11% in control plants (p<0.05, Tukey-B). As a consequence, percentage of leaves with more severe symptoms (categories 2-4) was significantly reduced in SB-treated plants compared to the control. One formulation (SB EC-2) at a concentration of 7.5 mg ml$^{-1}$ was even comparable to Limesulphur, the best organic reference treatment.

TABLE 8

Efficacy of two formulations of Siam benzoin (SB EC-1 and SB EC-2) at two concentrations (2.5 and 7.5 mg ml$^{-1}$) on apple seedlings cv. 'Jonagold' against *M. coronaria* under semi-controlled conditions, compared to efficacies of a copper (Bordeaux mixture, 0.6 mg ml$^{-1}$ $Cu^{2+}$) and a Limesulphur reference (6 mg ml$^{-1}$). Disease levels were categorized into 5 classes (Cat. 0: no disease; Cat. 1: 1-5 spots per leaf; Cat. 2: 6-20 spots per leaf, Cat. 3: 21-50 spots per leaf; Cat. 4: >50 spots per leaf) and the mean relative frequency of each disease class was calculated per plant. The table shows means of the six replicate plants per treatment. Different letters indicate significant differences between treatments of a category (Tukey-B, p < 0.05).

| | Mean | | | | | SD | | | | |
|---|---|---|---|---|---|---|---|---|---|---|
| Treatment | Cat 0 | Cat 1 | Cat 2 | Cat 3 | Cat 4 | Cat 0 | Cat 1 | Cat 2 | Cat 3 | Cat 4 |
| Control | 1 a | 10 a | 50 a | 32 a | 7 a | 4 | 13 | 13 | 16 | 9 |
| Bordeaux mixture | 11 ab | 47 bc | 38 ac | 4 b | 0 a | 12 | 23 | 26 | 5 | 0 |
| Limesulphur | 75 d | 25 ab | 0 b | 0 b | 0 a | 7 | 7 | 0 | 0 | 0 |
| SB EC-1 7.5 mg ml$^{-1}$ | 35 bc | 63 c | 2 b | 0 b | 0 a | 16 | 14 | 4 | 0 | 0 |

TABLE 8-continued

Efficacy of two formulations of Siam benzoin (SB EC-1 and SB EC-2) at two concentrations (2.5 and 7.5 mg ml$^{-1}$) on apple seedlings cv. 'Jonagold' against *M. coronaria* under semi-controlled conditions, compared to efficacies of a copper (Bordeaux mixture, 0.6 mg ml$^{-1}$ Cu$^{2+}$) and a Limesulphur reference (6 mg ml$^{-1}$). Disease levels were categorized into 5 classes (Cat. 0: no disease; Cat. 1: 1-5 spots per leaf; Cat. 2: 6-20 spots per leaf, Cat. 3: 21-50 spots per leaf; Cat. 4: >50 spots per leaf) and the mean relative frequency of each disease class was calculated per plant. The table shows means of the six replicate plants per treatment. Different letters indicate significant differences between treatments of a category (Tukey-B, p < 0.05).

| Treatment | Mean | | | | | SD | | | | |
|---|---|---|---|---|---|---|---|---|---|---|
| | Cat 0 | Cat 1 | Cat 2 | Cat 3 | Cat 4 | Cat 0 | Cat 1 | Cat 2 | Cat 3 | Cat 4 |
| SB EC-1 2.5 mg ml$^{-1}$ | 23 bc | 60 c | 17 bc | 0 b | 0 a | 20 | 20 | 15 | 0 | 0 |
| SB EC-2 7.5 mg ml$^{-1}$ | 54 cd | 44 abc | 2 b | 0 b | 0 a | 33 | 29 | 5 | 0 | 0 |
| SB EC-2 2.5 mg ml$^{-1}$ | 22 bc | 68 c | 11 bc | 0 b | 0 a | 21 | 16 | 11 | 0 | 0 |

2.3. Tomato—*P. infestans*.

Efficacy of Siam benzoin petroleum ether extract on tomato seedlings against *P. infestans* under semi-controlled conditions ranged between 89% and 100% at 2 mg ml$^{-1}$ and 63% and 100% at 1 mg ml$^{-1}$ (Table 9), and was even superior to the copper reference.

TABLE 9

Efficacy of Siam benzoin petroleum ether extract (SB-PE) (1 and 2 mg/ml) on tomato seedlings (cv. 'Marmande') against *P. infestans* under semi-controlled conditions, compared to efficacies of two concentrations of a copper reference treatment (Cu$^{2+}$ in the form of copper hydroxide, KOCIDE OPTI ®). The table shows results (means ± SD) of four independent experiments, each experiment with 6 replicate plants per treatment.

| | Efficacy (%) [1] | | | | Disease severity |
|---|---|---|---|---|---|
| | SB-PE | | Cu$^{2+}$ | | non-treated control |
| | Product Concentration (mg ml$^{-1}$) | | | | |
| | 2 | 1 | 0.3 | 0.03 | (%) [2] |
| Exp_1 | 89 ± 20 | | 87 ± 12 | 57 ± 25 | 67 ± 10 |
| Exp_2 | 92 ± 4 | 63 ± 21 | 75 ± 23 | 59 ± 28 | 85 ± 9 |
| Exp_3 | 100 ± 0 | 100 ± 0 | 72 ± 23 | 75 ± 17 | 93 ± 13 |
| Exp_4 | 93 ± 10 | 87 ± 10 | 95 ± 6 | 63 ± 16 | 68 ± 5 |
| Mean [3] | 94 ± 5 | 83 ± 19 | 82 ± 11 | 64 ± 8 | 78 ± 13 |

[1] Percentage reduction in the diseased leaf area in treated plants compared to the non-treated control;
[2] Percentage leaf area with disease symptoms;
[3] Mean and SD of all independent experiments Example 3

Fungicidal Activity of Siam Benzoin on Grapevine Against Downy Mildew Caused by *P. viticola* and Powdery Mildew Caused by *Oidium tuckeri* Under Field Conditions 3.1 Downy Mildew (*P. viticola*)

3.1.1. Disease Development:

In 2014, disease pressure of downy mildew caused by *P. viticola* was relatively low in the primary season due to the warm and dry weather conditions from Mid-May until end of June. The first major infection period for downy mildew occurred at the beginning of June 2014 and resulted in few first lesions in Mid-June. During August 2014, downy mildew developed rapidly such that by the end of August, disease incidence was up to 100% and severity about 50% (Table 10). Treatments with a high incidence of powdery mildew showed a low rate of downy mildew sporulation on leaves. In these cases the symptoms directly developed into mosaic- and later necrotic spots.

In 2015, the first visible downy mildew symptoms appeared in the beginning of June. Until the end of June 2015, the degree of infection progressed quite rapidly. The warm and dry weather conditions during July and August 2015 slowed down the infection progress. By the end of August 2015, the disease incidence reached approx. 50% and disease severity approx. 9% in the untreated control (Table 11).

3.1.2 Efficacy of Test Products

In both seasons, the standard fungicide program as recommended for Swiss organic grapevine production as well as the copper control protected leaves and fruit very efficiently from downy and powdery mildew (>92% efficacy with 16 treatments).

In both seasons, Siam benzoin showed a significant effect against downy mildew at the end of the season. In 2014, Siam benzoin petroleum ether extract (SB-PE) reduced disease severity on leaves by 31% at the end of the season (Table 10). In 2015, Siam benzoin (SB) reduced downy mildew disease incidence and severity compared to the non-treated control throughout the whole season, and differences became significant on the last disease assessment mid of August, with efficacies between 64% and 68% (Table 11). On grapes, downy mildew disease severity was reduced by Siam benzoin up to 87% in 2015 (Table 12). In 2014, late occurrence of downy mildew (after powdery mildew infections) did not allow for a downy mildew disease assessment on grapes. Yet, overall damage on grapes caused by both diseases was reduced by 43% on plants treated with Siam benzoin petroleum ether extract as compared to non-treated control plants (Table 13).

TABLE 10

Disease development (severity) of downy mildew caused by *P. viticola* under field conditions in 2014 on leaves of untreated grapevine plants (Control) and plants treated with Siam benzoin petroleum ether extract (SB-PE) (1 g l$^{-1}$), copper (0.3 g l$^{-1}$ Cu$^{2+}$ in the form of copper hydroxide, KOCIDE OPTI ®) or a plant protection strategy recommended by the FiBL-advisory service to Swiss grapevine producers ('Strategy'). Disease severity was assessed on three dates: 5 Aug. 2014 (Table 10A), 19 August (Table 10B), 27 August (Table 10C).

| | 10A | | | |
|---|---|---|---|---|
| | 5 Aug. 2014 | | | |
| | Severity (%) | | | |
| Treatment | Mean [a] | SD [a] | Efficacy (%) [c] | Tukey-B [b] |
| untreated | 4.1 | 2.0 | — | A |
| copper | 0.1 | 0.0 | 97.7 | B |

TABLE 10-continued

Disease development (severity) of downy mildew caused by *P. viticola* under field conditions in 2014 on leaves of untreated grapevine plants (Control) and plants treated with Siam benzoin petroleum ether extract (SB-PE) (1 g l$^{-1}$), copper (0.3 g l$^{-1}$ Cu$^{2+}$ in the form of copper hydroxide, KOCIDE OPTI ®) or a plant protection strategy recommended by the FiBL-advisory service to Swiss grapevine producers ('Strategy'). Disease severity was assessed on three dates: 5 Aug. 2014 (Table 10A), 19 August (Table 10B), 27 August (Table 10C).

| | | | | |
|---|---|---|---|---|
| ref. strategy | 0.1 | 0.1 | 97.6 | B |
| SB-PE | 2.7 | 0.9 | 32.2 | A |

10B

19 Aug. 2014

| Treatment | Severity (%) Mean [a] | SD [a] | Efficacy (%) [c] | Tukey-B [b] |
|---|---|---|---|---|
| untreated | 22.3 | 5.7 | — | A |
| copper | 1.3 | 0.4 | 94.0 | B |
| ref. strategy | 1.9 | 1.0 | 91.6 | B |
| SB-PE | 12.6 | 1.3 | 43.7 | C |

10C

27 Aug. 2014

| Treatment | Severity (%) Mean [a] | SD [a] | Efficacy (%) [c] | Tukey-B [b] |
|---|---|---|---|---|
| untreated | 50.7 | 10.8 | — | A |
| copper | 3.1 | 0.7 | 93.9 | B |
| ref. strategy | 3.4 | 1.4 | 93.4 | B |
| SB-PE | 35.2 | 6.3 | 30.5 | C |

[a] means and standard deviations (SD) of four treatment replicates.
[b] Different letters indicate significant differences between treatments
[c] Efficacy calculated according to Abbott in %

TABLE 11

Disease development (severity) of downy mildew caused by *P. viticola* under field conditions in 2014 on leaves of untreated grapevine plants (Control) and plants treated with copper (0.3 g l$^{-1}$ Cu$^{2+}$ in the form of copper hydroxide, KOCIDE OPTI ®), a plant protection strategy recommended by the FiBL-advisory service to Swiss grapevine producers ('Strategy') or two formulations based on Siam benzoin resin (SB WP and SB EC) (2 g l$^{-1}$ extract). Disease severity was assessed on four dates: 26 Jun. 2015 (Table 11A), 3 Jul. 2015 (Table 11B), 24 Jul. 2015 (Table 11C), and 18 Aug. 2015 (Table 11D).

11A

26 Jun. 2015

| Treatment | Severity (%) Mean [a] | SD [a] | Efficacy (%) [c] | Tukey-B [b] |
|---|---|---|---|---|
| Control | 2.8 | 4.7 | | A |
| Copper | 0.3 | 0.3 | 90.0 | A |
| Strategy | 0.2 | 0.2 | 93.9 | A |
| SB WP | 1.4 | 1.7 | 51.1 | A |
| SB EC | 1.0 | 0.9 | 65.7 | A |

TABLE 11-continued

Disease development (severity) of downy mildew caused by *P. viticola* under field conditions in 2014 on leaves of untreated grapevine plants (Control) and plants treated with copper (0.3 g l$^{-1}$ Cu$^{2+}$ in the form of copper hydroxide, KOCIDE OPTI ®), a plant protection strategy recommended by the FiBL-advisory service to Swiss grapevine producers ('Strategy') or two formulations based on Siam benzoin resin (SB WP and SB EC) (2 g l$^{-1}$ extract). Disease severity was assessed on four dates: 26 Jun. 2015 (Table 11A), 3 Jul. 2015 (Table 11B), 24 Jul. 2015 (Table 11C), and 18 Aug. 2015 (Table 11D).

11B

3 Jul. 2015

| Treatment | Severity (%) Mean [a] | SD [a] | Efficacy (%) [c] | Tukey-B [b] |
|---|---|---|---|---|
| Control | 3.0 | 3.1 | 0.0 | A |
| Copper | 0.6 | 0.3 | 79.9 | B |
| Strategy | 0.6 | 0.5 | 81.0 | B |
| SB WP | 1.5 | 0.9 | 50.3 | AB |
| SB EC | 1.1 | 0.6 | 61.8 | AB |

11C

24 Jul. 2015

| Treatment | Severity (%) Mean [a] | SD [a] | Efficacy (%) [c] | Tukey-B [b] |
|---|---|---|---|---|
| Control | 5.0 | 4.0 | | A |
| Copper | 1.2 | 0.6 | 75.8 | BC |
| Strategy | 0.9 | 0.6 | 82.6 | B |
| SB WP | 3.5 | 1.7 | 30.1 | AC |
| SB EC | 2.5 | 1.3 | 49.2 | ABC |

11D

18. Aug. 2015

| Treatment | Severity (%) Mean [a] | SD [a] | Efficacy (%) [c] | Tukey-B [b] |
|---|---|---|---|---|
| Control | 8.7 | 5.9 | | A |
| Copper | 1.0 | 0.4 | 88.3 | B |
| Strategy | 0.9 | 0.6 | 89.9 | B |
| SB WP | 3.1 | 2.1 | 64.2 | B |
| SB EC | 2.8 | 1.8 | 68.1 | B |

[a] means and standard deviations (SD) of four treatment replicates.
[b] Different letters indicate significant differences between treatments
[c] Efficacy calculated according to Abbott in %

TABLE 12

Downy mildew disease severity under field conditions in 2015 on grapes of non-treated plants (Control) and on grapes of plants treated with copper (0.3 g l$^{-1}$ Cu$^{2+}$ in the form of copper hydroxide, KOCIDE OPTI®), a plant protection strategy recommended by the FiBL-advisory service to Swiss grapevine producers ('Strategy') or two formulations based on Siam benzoin (SB WP and SB EC) (2 g l$^{-1}$ Siam benzoin).

| | Incidence (%) | | | | Severity (%) | | | |
|---|---|---|---|---|---|---|---|---|
| | Mean[a] | SD[a] | Tukey[b] | Efficacy (%)[c] | Mean[a] | SD[a] | Tukey[b] | Efficacy (%)[c] |
| Control | 51.4 | 25 | B | | 19.9 | 22.7 | B | |
| Copper | 20.6 | 11.3 | AB | 59.9 | 1.2 | 1.3 | A | 93.9 |
| Strategy | 9.3 | 6.8 | A | 81.9 | 1.8 | 3.4 | A | 90.7 |
| SB WP | 8.4 | 5.7 | A | 83.6 | 0.8 | 1.3 | A | 96.2 |
| SB EC | 18.3 | 14.9 | AB | 64.3 | 2.5 | 3.4 | AB | 87.2 |

[a] means and standard deviations (SD) of four treatment replicates.
[b] Different letters indicate significant differences between treatments
[c] Efficacy calculated according to Abbott in %

TABLE 13

Overall damage caused by downy and powdery mildew under field conditions in 2014 on grapes of non-treated grapevine plants (Control) and on plants treated with copper (0.3 g l$^{-1}$ Cu$^{2+}$ in the form of copper hydroxide, KOCIDE OPTI®), a plant protection strategy recommended by the FiBL-advisory service to Swiss grapevine producers ('Strategy') or a Siam benzoin petroleum ether extract (SB-PE) (1 g l$^{-1}$).

| | Severity (%) | | | |
|---|---|---|---|---|
| | Mean[a] | SD[a] | Tukey[b] | Efficacy |
| Control | 76.3 | 21.6 | A | |
| Copper | 3.3 | 1.1 | B | 95.7 |
| Strategy | 3.8 | 1.3 | B | 95.1 |
| SB-PE | 43.8 | 19.8 | C | 42.6 |

[a] means and standard deviations (SD) of four treatment replicates.
[b] Different letters indicate significant differences between treatments
[c] Efficacy calculated according to Abbott in %

3.2 Powdery Mildew (*Oidium tuckeri*)

3.2.1 Disease Development:

In both seasons (2014 and 2015), there was unusually high disease pressure by powdery mildew caused by *Oidium tuckeri*, resulting in 67% (2014) or approx. 30% (2015) powdery mildew disease severity on leaves and 56% (2014) or 60% (2015) disease incidence on grapes (Tables 14A and 14B).

3.2.2 Efficacy of Test Products:

In both seasons, the standard fungicide program as recommended for Swiss organic grapevine production as well as the copper control protected leaves and fruit very efficiently from powdery mildew (>90% efficacy) (Tables 14A and 14B).

In both seasons, SB-PE showed good efficacy against powdery mildew. Powdery mildew disease severity on leaves was reduced by 66% in 2014 (Table 14A) and by 75 and 86% in 2015 (Table 14B), while efficacy on grapes was 51% in 2014 and 30% in 2015.

TABLE 14A

Powdery mildew disease under field conditions in 2014 (on leaves and grapes of non-treated plants (Control) and plants treated with copper (0.3 g l$^{-1}$ Cu$^{2+}$ in the form of copper hydroxide, KOCIDE OPTI®), a plant protection strategy recommended by the FiBL-advisory service to Swiss grapevine producers ('Strategy') or by Siam benzoin (Siam benzoin petroleum ether extract, 1 g l$^{-1}$).

| | 2014 | | | | | | | |
|---|---|---|---|---|---|---|---|---|
| | Leaves Severity (%) | | | | Grapes (Incidence %) | | | |
| | Mean[a] | SD[a] | Tukey[b] | Efficacy[c] | Mean[a] | SD[a] | Tukey[b] | Efficacy[c] |
| Control | 67.3 | 11.7 | A | | 55.7 | 21.0 | B | — |
| Copper | 0.0 | 0.0 | B | 100.0 | 4.6 | 4.3 | A | 91.8 |
| Strategy | 0.0 | 0.0 | B | 100.0 | 3.5 | 0.6 | A | 93.7 |
| SB-PE | 23.0 | 17.5 | C | 65.8 | 27.5 | 24.5 | AB | 50.7 |

[a] means and standard deviations (SD) of four treatment replicates.
[b] Different letters indicate significant differences between treatments
[c] Efficacy calculated according to Abbott in %

TABLE 14B

Powdery mildew disease under field conditions in 2015 (on leaves and grapes of non-treated plants (Control) and plants treated with copper (0.3 g l$^{-1}$ Cu$^{2+}$ in the form of copper hydroxide, KOCIDE OPTI®), a plant protection strategy recommended by the FiBL-advisory service to Swiss grapevine producers ('Strategy') or by Siam benzoin (two formulations of Siam benzoin: SB WP and SB EC, 2 g l$^{-1}$ Siam benzoin).

|  | 2015 | | | | | | | |
|---|---|---|---|---|---|---|---|---|
|  | Severity classes (0-3)$^d$ | | | | Grapes (Incidence %) | | | |
|  | Mean$^a$ | SD$^a$ | Tukey$^b$ | Efficacy$^c$ | Mean$^a$ | SD$^a$ | Tukey$^b$ | Efficacy$^c$ |
| Control | 2.6 | 0.3 | A |  | 60.0 | 19.6 | B |  |
| Copper | 0.0 | 0.0 | B | 100.0 | 15.4 | 10.8 | AB | 74.3 |
| Strategy | 0.1 | 0.3 | BC | 95.1 | 18.3 | 21.3 | AB | 69.5 |
| SB WP | 0.4 | 0.2 | BC | 86.3 | 41.7 | 44.1 | AB | 30.5 |
| SB EC | 0.6 | 0.3 | C | 74.8 | 42.9 | 24.0 | AB | 28.5 |

$^a$means and standard deviations (SD) of four treatment replicates.
$^b$Different letters indicate significant differences between treatments
$^c$Efficacy calculated according to Abbott in %
$^d$four disease classes: 0: no symptoms; 1: low disease level (<10% of leaves show 1-2 colonies); 2: intermediate disease level (>10% of leaves show symptoms/more than 2 colonies on leaves); 3: high disease level (predominantly old necrotic spots /symptoms through all leaf ages).

Example 4

Fungicidal Activity of Balsam of Peru In Vitro and on Grapevine and Apple Seedlings Against *P. viticola* and *V. inaequalis* and Identification of the Active Ingredient MIC$_{100}$ of Balsam of Peru in vitro was 16 μg ml$^{-1}$ against *P. viticola* and was thus comparable to Siam benzoin (SB) and Sumatra benzoin (SumB) (Tab. 2). MIC$_{100}$ against *V. inaequalis* and *P. infestans* were between 250 and 500 μg ml$^{-1}$. Balsam of Peru efficiently protected grapevine seedlings against *P. viticola* (efficacy of 90% at a concentration of 1 mg ml$^{-1}$) and apple seedlings against *V. inaequalis* (efficacy of 97% at 2.5 mg ml$^{-1}$) (Tab. 16). Efficacy was comparable to a copper reference.

HPLC analysis of Balsam of Peru showed the presence of a major peak in the UV chromatogram. The compound was isolated by preparative HPLC and identified as benzyl cinnamate (compound 3) by comprehensive NMR analysis, and ESI mass spectrometry. Benzyl cinnamate (BC) was very active against *P. viticola* in in vitro experiments, with MIC$_{100}$ of 8 μg ml$^{-1}$(Tab. 15).

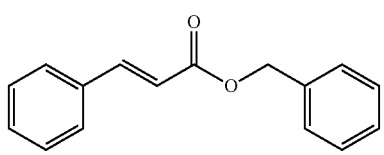

3

TABLE 15

Minimal inhibitory concentrations (MIC$_{100}$) of Balsam of Peru (BP) and benzyl cinnamate (BC) against *Plasmopara viticola*, *Venturia inaequalis* and *Phytophthora infestans*.

|  | MIC$_{100}$ | | |
|---|---|---|---|
|  | *P. viticola* | *V. inaequalis* | *P. infestans* |
| BP | 16$^a$ | 500 | 250 |
| BC | 8 | >500 | 500 |

$^a$μg ml$^{-1}$

TABLE 16

Efficacy of Balsam of Peru dissolved in DMSO (BP-DMSO) and a copper reference (Cu$^{2+}$ in the form of copper hydroxide, KOCIDE OPTI®) against *Plasmopara viticola* on grapevine cv. 'Chasselas' seedlings and against *Venturia inaequalis* on apple cv. 'Jonagold' seedlings under semi-controlled conditions. The table shows means ± SD (n = 6). Disease severity (percentage leaf area with disease symptoms) of the non-treated control was 84% ± 12% (*P. viticola*) or 20% ± 12% (*V. inaequalis*)

| Treatment | Conc (mg ml$^{-1}$) | Efficacy (%) ± SD | |
|---|---|---|---|
|  |  | *P. viticola* | *V. inaequalis* |
| Cu$^{2+}$ | 0.3 | 87 ± 9 | 91 ± 6 |
|  | 0.03 | 52 ± 24 | 50 ± 43 |
| BP-DMSO | 2.5 | 90 ± 12 | 97 ± 5 |
|  | 1 | 90 ± 9 | 57 ± 61 |
|  | 0.25 | 18 ± 19 | 19 ± 69 |

The invention claimed is:

1. A method of controlling a fungal infection in a plant, plant propagation material or soil in need thereof, comprising applying an effective amount of a composition to said plant, said plant propagation material or said soil, wherein said composition comprises at least one compound of formula (II)

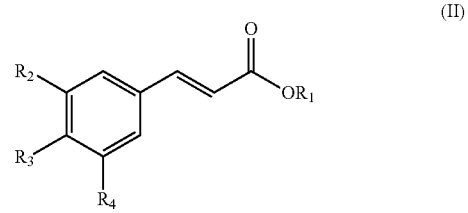

(II)

wherein

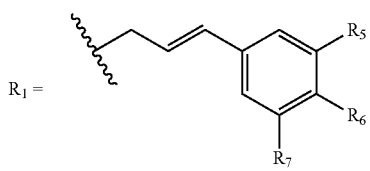

wherein
R$_2$, R$_3$, R$_4$, R$_5$, R$_6$ and R$_7$ are independently of each other H, OH or OCH$_3$, wherein at least one of said R$_5$, R$_6$ and R$_7$ is not H.

2. The method according to claim 1, wherein R$_2$, R$_3$ and R$_4$ are each H.

3. The method according to claim 1, wherein said at least one compound of formula (II) is 2 (p-coumaryl cinnamate):

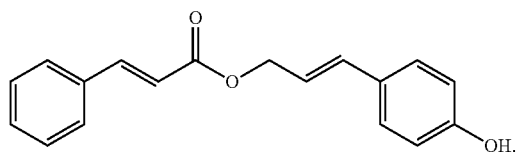

4. The method according to claim 1, wherein said at least one compound of formula (II) is present as a constituent of a plant extract.

5. The method according to claim 4, wherein said at least one plant extract is an extract from a plant of the family of Styracaceae.

6. The method according to claim 4, wherein said at least one plant extract is an extract from a plant of the genus *Styrax*, and wherein said plant of the genus *Styrax* is selected from the species *Styrax tonkinensis, Styrax benzoin, Styrax paralleloneurum, Styrax hypoglauca* and *Styrax cascarifolia* or a subspecies or variety thereof.

7. The method according to claim 4, wherein said at least one plant extract is an extract of a resin of said plant.

8. The method according to claim 1, wherein the fungal infection is caused by a plant fungal pathogen selected from the group consisting of (i) oomycetes, (ii) ascomycetes and (iii) basidiomycetes.

9. The method according to claim 8, wherein said fungal infection is a fungal infection of a crop selected from a fruit crop or a vegetable.

10. The method according to claim 1, wherein said composition is in a formulation, wherein said formulation is selected from a wettable powder, an emulsifiable concentrate, a water-dispersible granule, an emulsifiable granule, a microemulsion concentrate, an oil-in-water or water-in-oil emulsion, a suspo-emulsion and a capsule suspension.

11. The method according to claim 1, wherein at most two of R$_5$, R$_6$ and R$_7$ are independently of each other OH or OCH$_3$.

12. The method according to claim 4, wherein said at least one plant extract is an extract of a resin of Siam benzoin or Sumatra benzoin.

13. The method according to claim 5, wherein said at least one plant extract is an extract of *Styrax tonkinensis, Styrax benzoin, Styrax paralleloneurum*.

14. A fungicidal composition, wherein said composition comprises at least one compound of formula (II)

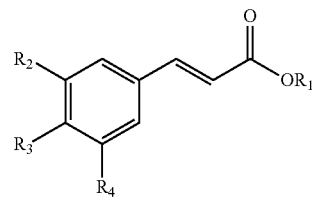

wherein

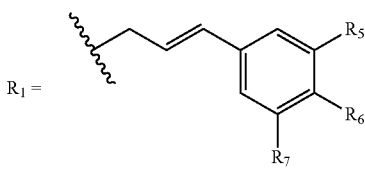

wherein
R$_2$, R$_3$, R$_4$, R$_5$, R$_6$ and R$_7$ are independently of each other H, OH or OCH$_3$, wherein at least one of said R$_5$, R$_6$ and R$_7$ is not H.

15. The fungicidal composition according to claim 14, wherein said fungicidal composition further comprises a fungicidally acceptable carrier, emulsifier, adjuvant or diluent.

16. The method according to claim 1, wherein R$_6$ is OH.

17. The method according to claim 1, wherein R$_7$ is OCH$_3$.

18. The method according to claim 8, wherein said (i) oomycetes are selected from the genera *Hyaloperonospora, Peronospora, Plasmopara, Bremia, Pseudoperonospora* and *Phytophthora*; and wherein said (ii) ascomycetes are selected from the genera *Alternaria, Guignardia, Venturia, Oidium, Erysiphe, Sphaeroteca, Leveillula, Podosphaeria, Marssonina, Taphrina, Septoria, Sclerotinia, Pseudocercosporella, Botrytis, Phomopsis, Pyrenospora; Helminthosporium, Drechslera* and *Pyrenophora*; and wherein said (iii) basidiomycetes are selected from the genera *Puccinia, Phacopsora*, and *Rhizoctonia*.

19. The fungicidal composition according to claim 14, wherein said at least one compound of formula (II) is 2 (p-coumaryl cinnamate)

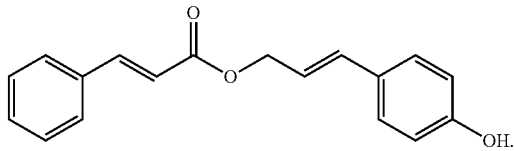

20. The composition according to claim 14, wherein at least one compound of formula (II) is present as a constituent of a plant extract.

21. The method according to claim 3, wherein said method is a method of controlling a fungal infection in a plant.

22. The method according to claim 21, wherein the fungal infection is caused by a plant fungal pathogen selected from the group consisting of (i) oomycetes.

23. The method according to claim 22, wherein said (i) oomycetes are selected from the genera *Hyaloperonospora, Peronospora, Plasmopara, Bremia, Pseudoperonospora* and *Phytophthora*.

24. The method according to claim 22, wherein said (i) oomycetes are selected from the genera *Plasmopara, Pseudoperonospora* and *Phytophthora*.

25. The method according to claim 4, wherein said at least one compound of formula (II) is 2 (p-coumaryl cinnamate):

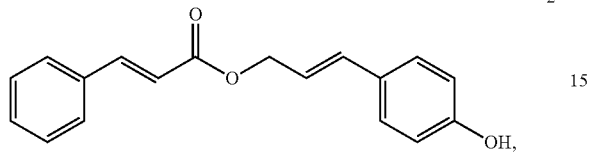

2 and wherein said at least one plant extract is an extract from a plant of the genus Styrax, and wherein said plant of the genus Styrax is selected from the species *Styrax tonkinensis, Styrax benzoin, Styrax paralleloneurum*, or a subspecies or variety thereof.

26. The method according to claim 25, wherein said plant of the genus Styrax is selected from the species *Styrax benzoin* and *Styrax paralleloneurum*.

* * * * *